(12) United States Patent
Purohit

(10) Patent No.: US 9,820,760 B2
(45) Date of Patent: Nov. 21, 2017

(54) AIMING DEVICE FOR DISTAL LOCKING OF INTRAMEDULLARY NAILS AND METHODS OF USE

(71) Applicant: DePuy Synthes Products, Inc., Raynham, MA (US)

(72) Inventor: Hitendra Purohit, Mumbai (IN)

(73) Assignee: DePuy Synthes Products, Inc., Raynham, MA (US)

( * ) Notice: Subject to any disclaimer, the term of this patent is extended or adjusted under 35 U.S.C. 154(b) by 392 days.

(21) Appl. No.: 14/695,760

(22) Filed: Apr. 24, 2015

(65) Prior Publication Data

US 2015/0305791 A1    Oct. 29, 2015

(51) Int. Cl.
*A61B 17/88*  (2006.01)
*A61B 19/00*  (2006.01)
*A61B 17/72*  (2006.01)
*A61B 17/17*  (2006.01)
*A61B 17/16*  (2006.01)
*A61B 5/06*   (2006.01)
*A61B 17/68*  (2006.01)
*A61B 17/90*  (2006.01)

(52) U.S. Cl.
CPC .......... *A61B 17/1707* (2013.01); *A61B 5/062* (2013.01); *A61B 17/162* (2013.01); *A61B 17/1725* (2013.01); *A61B 17/72* (2013.01); *A61B 17/8872* (2013.01); *A61B 2017/681* (2013.01); *A61B 2017/90* (2013.01)

(58) Field of Classification Search
CPC . A61B 17/1725; A61B 17/1707; A61B 5/062; A61B 17/72; A61B 17/8872
See application file for complete search history.

(56) References Cited

U.S. PATENT DOCUMENTS

| | | | | |
|---|---|---|---|---|
| 4,667,664 A | * | 5/1987 | Taylor | A61B 17/1703 606/64 |
| 4,865,025 A | * | 9/1989 | Buzzi | A61B 17/1703 606/96 |
| 6,093,192 A | * | 7/2000 | Abel | A61B 17/1725 606/98 |
| 7,753,913 B2 | * | 7/2010 | Szakelyhidi, Jr. | A61B 5/06 606/96 |
| 2003/0135211 A1 | * | 7/2003 | Cho | A61B 17/1725 606/62 |

* cited by examiner

*Primary Examiner* — Christian Sevilla
(74) *Attorney, Agent, or Firm* — Wayne C. Jaeschke, Jr.

(57) ABSTRACT

An aiming device system that is configured to align at least one bone anchor guide to a first distal hole of an intramedullary nail can include an aiming arm that is configured to be operatively coupled to the intramedullary nail and an aiming guide. The aiming arm can define a sliding support that is elongate along a first direction. The aiming guide can include a guide body that defines at least a first bone anchor guide. The aiming guide is attached to the aiming arm such that the aiming guide is selectably movable along the sliding support, and selectably rotatable relative to the aiming arm. When the first bone anchor guide is retaining the guide sleeve, at least one of the selectable movement and selectable rotation of the guide body at least partially aligns the first bone anchor guide with the first distal hole of the intramedullary nail.

13 Claims, 17 Drawing Sheets

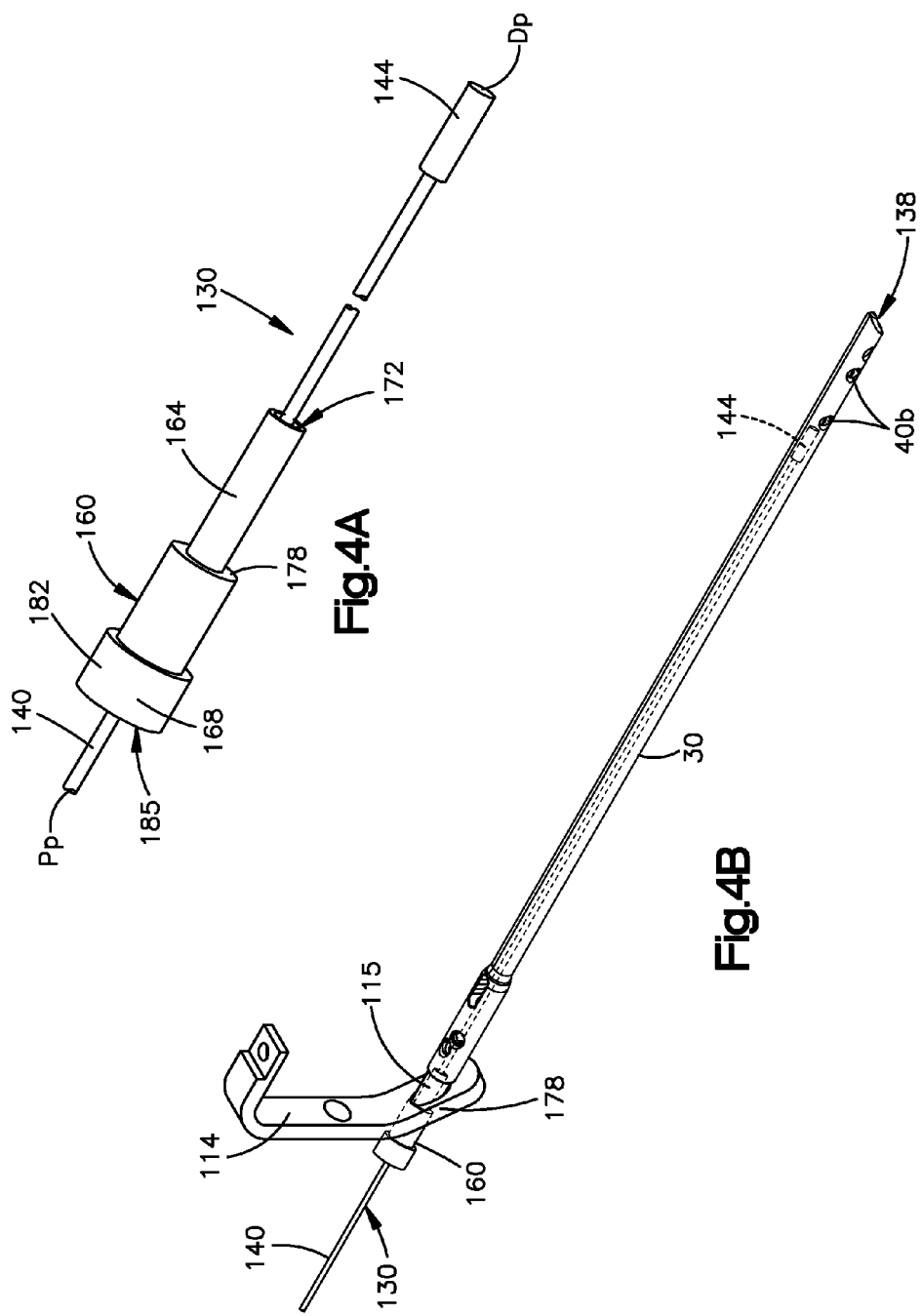

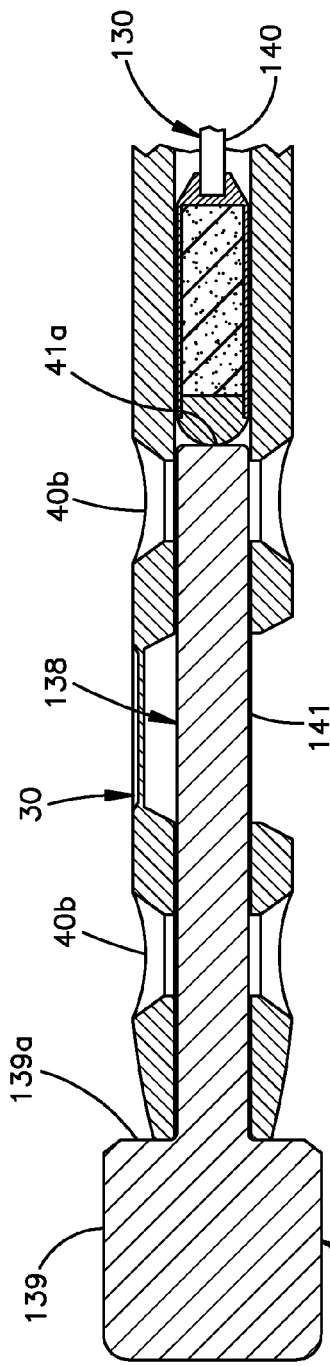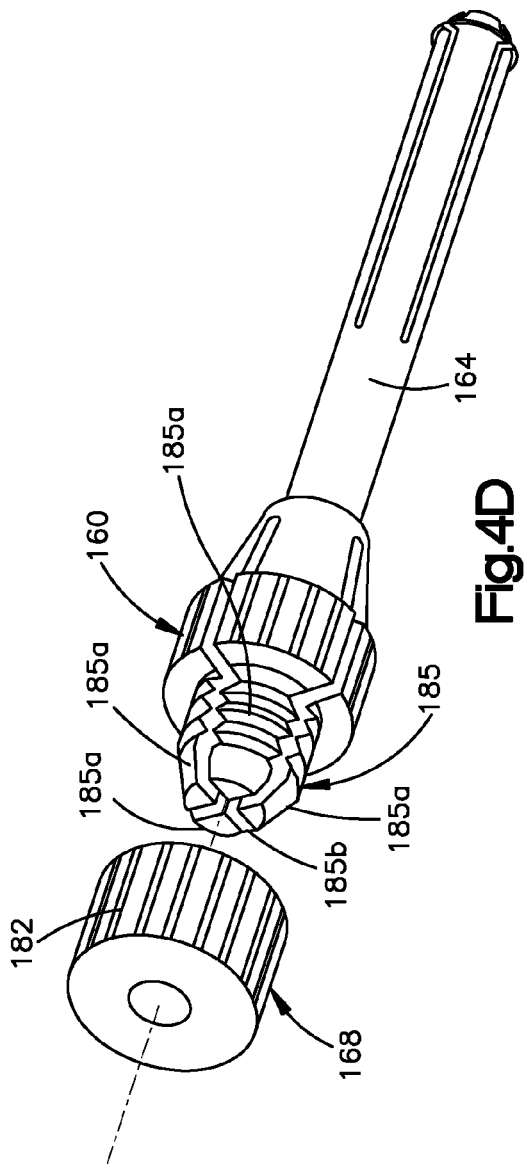
Fig.4C
Fig.4D

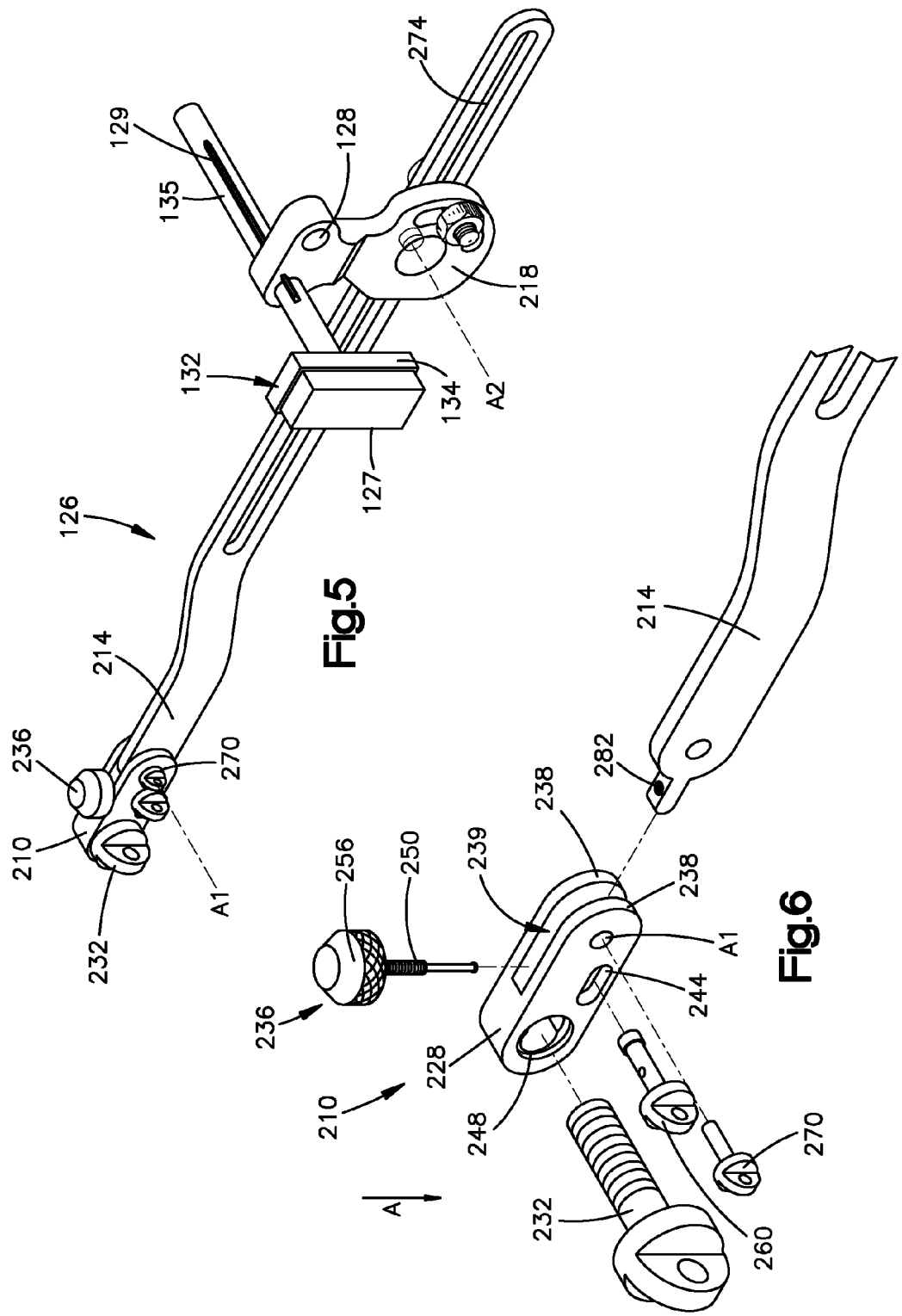

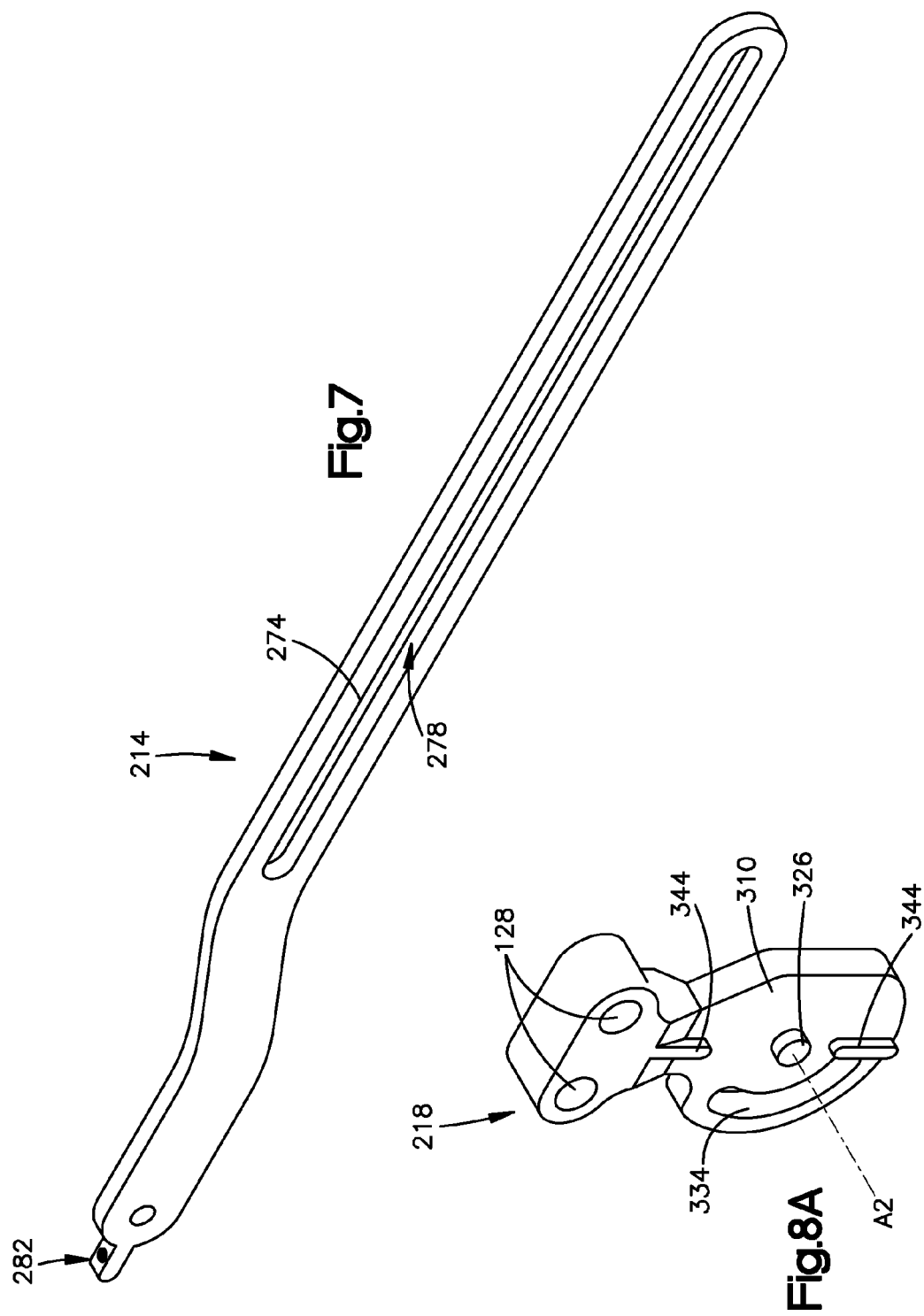

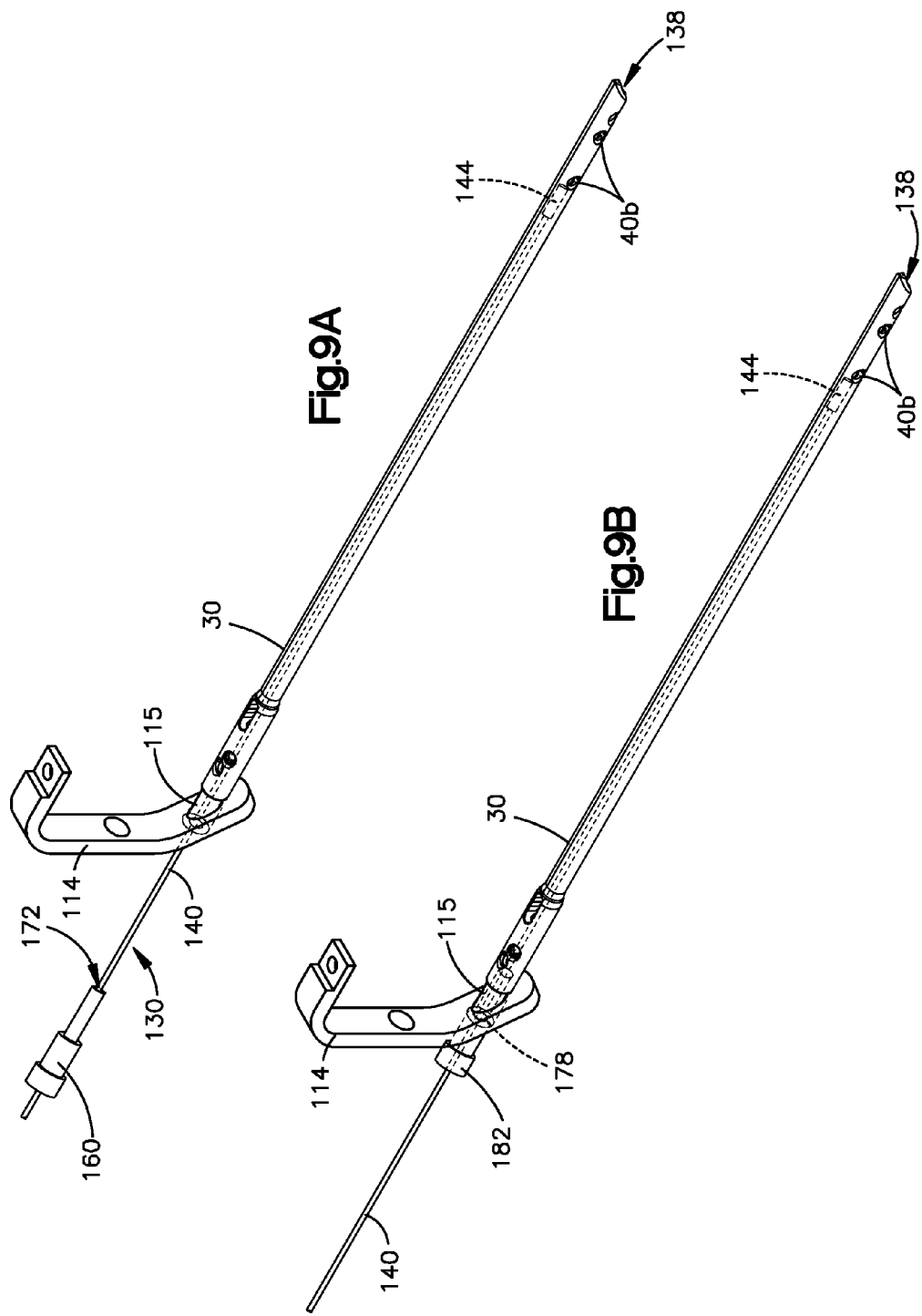

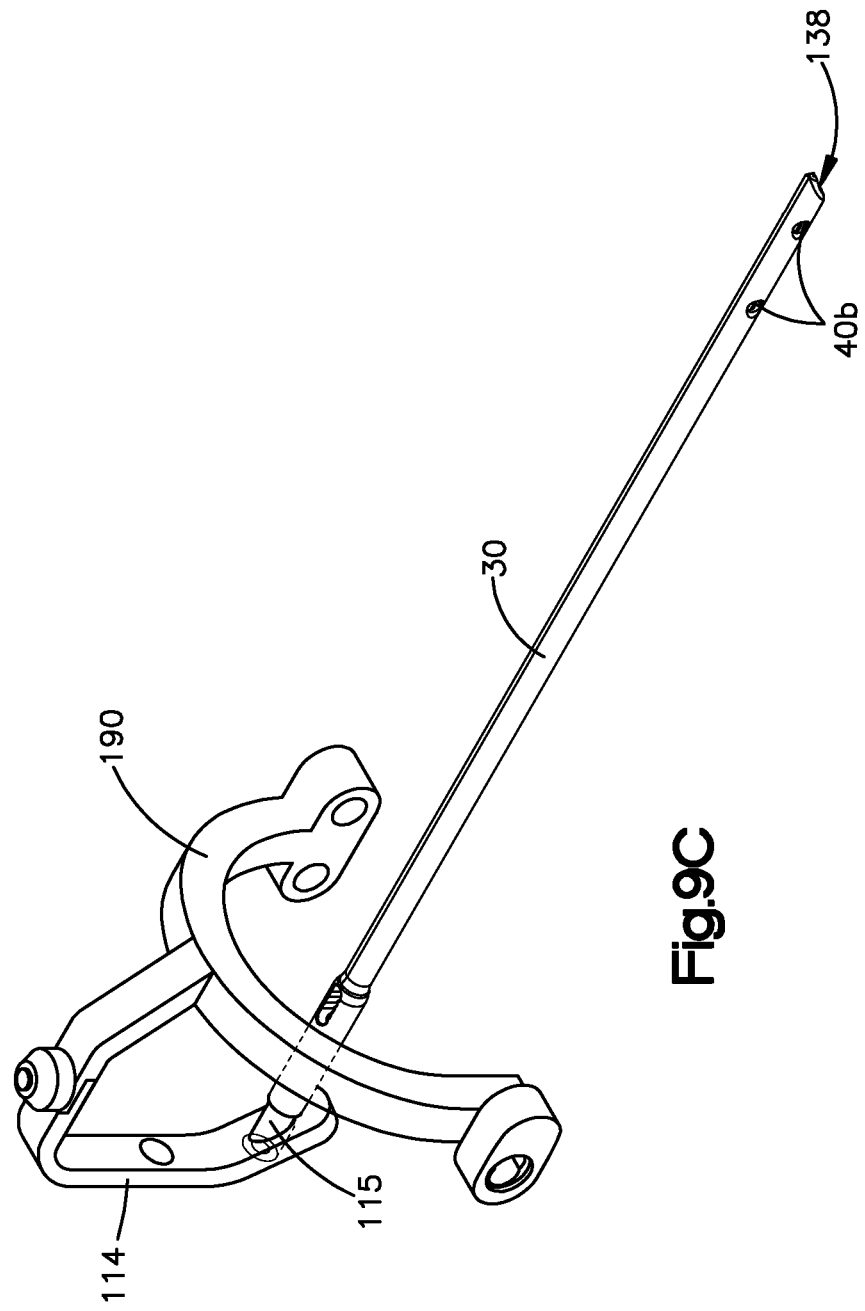

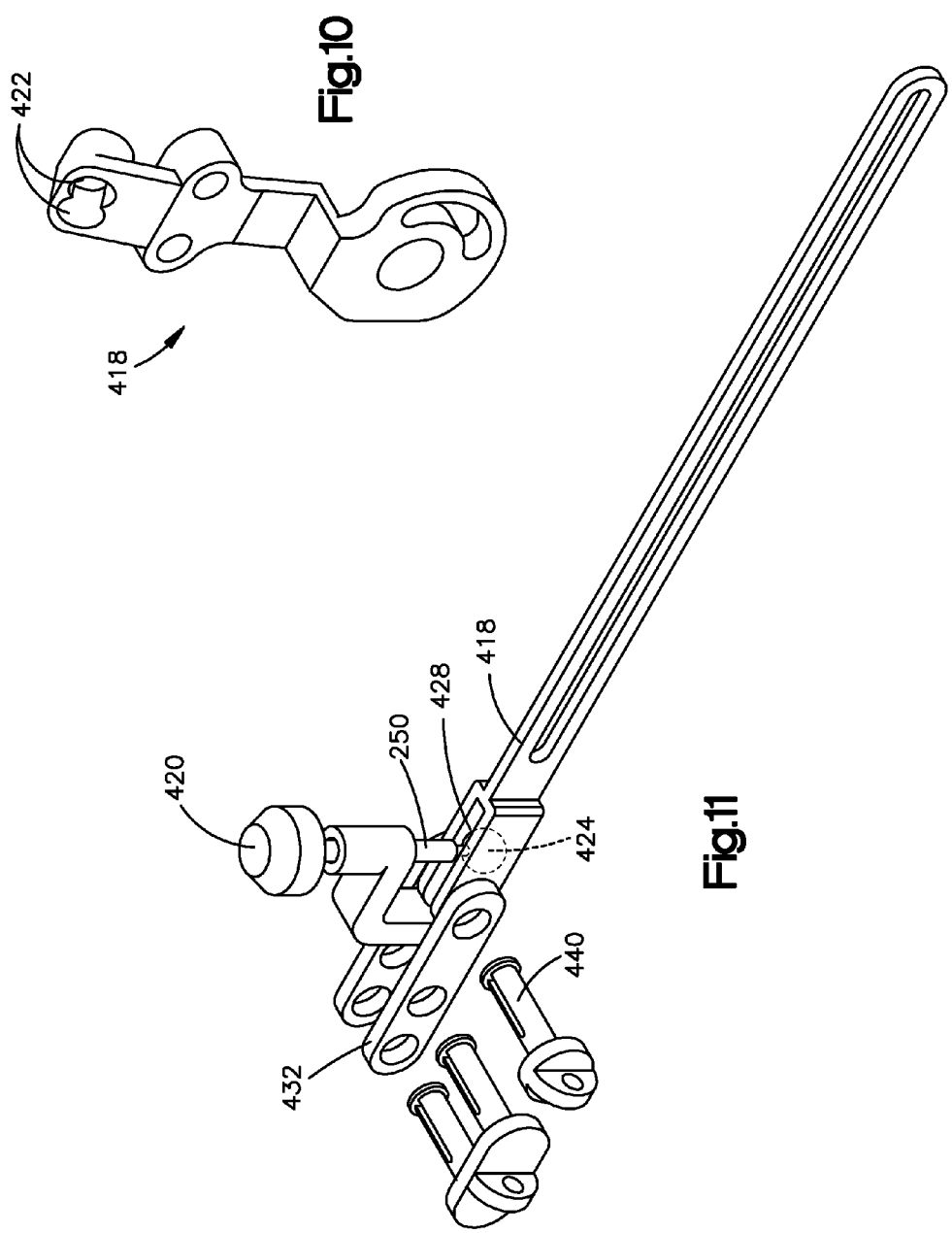

AIMING DEVICE FOR DISTAL LOCKING OF INTRAMEDULLARY NAILS AND METHODS OF USE

CROSS-REFERENCE TO RELATED APPLICATIONS

This claims priority to Indian Patent Application Serial No. 1131/DEL/2014, filed on Apr. 25, 2014, the disclosure of which is hereby incorporated by reference as if set forth in its entirety herein. The present application further incorporates by reference the disclosure of PCT Patent Application Serial No. PCT/US15/27434, filed Apr. 24, 2015, as if set forth in its entirety herein.

BACKGROUND

Intramedullary (IM) nails have been used for fixation of fractures in long bones especially in the femur, tibia, and humerus bones. These nails are locked in position by locking screws at proximal and distal ends through holes provided in the nail. Due to the varying anatomy of the medullary canal, the nail often deforms when it is inserted inside the canal and often poses a challenge to the surgeon in correctly locating the distal holes. Typically X-rays are used to visualize the holes and the surgeon performs drilling free-hand. X-rays, however, are not ideal as they expose individuals to radiation, consume time, and may not be very accurate due to free hand drilling.

Aiming instruments that are capable of locating the distal holes without X-rays are known. Such an aiming instrument is shown and described in U.S. Publication No. 2013/0018381. Such instruments include a source unit that is inserted inside the cannulated IM nail and a sensor that needs to be positioned at a certain relative location with respect to the source unit in order to determine the location of the distal holes. Adjusting the sensor to the desired position, however, can be difficult.

SUMMARY

In one embodiment, an aiming device system that is configured to align at least one bone anchor guide to a first distal hole of an intramedullary nail can comprise an aiming arm that is configured to be operatively coupled to the intramedullary nail and an aiming guide. The aiming arm can define a sliding support that is elongate along a first direction. The aiming guide can include a guide body that defines at least a first bone anchor guide that is configured to retain a first guide sleeve, the aiming guide further including an attachment mechanism that is configured to mate with the sliding support to thereby attach the guide body to the aiming arm such that the guide body is (i) selectably movable along the sliding support along the first direction, and (ii) selectably rotatable relative to the aiming arm about a guide body axis that is perpendicular to the first direction. When the first bone anchor guide is retaining the first guide sleeve, at least one of the selectable movement and selectable rotation of the guide body at least partially aligns the first bone anchor guide with the first distal hole of the intramedullary nail.

Also disclosed is a probe calibration system for an intramedullary nail aiming system in accordance with an embodiment. The probe calibration system can comprise a probe that is elongate along a first direction and defines a distal end and a proximal end that is spaced from the distal end along the first direction. The probe can include a flexible shaft that is elongate along the first direction and a source unit coupled to the flexible shaft. The source unit can be sized such that the source unit is translatable within a channel defined by an intramedullary nail and can be configured to emit a signal that is received by a sensor unit. The system can further comprise a probe retention member that includes an elongate body and a coupler attached to the elongate body. The probe retention member can define a bore that extends through both the elongate body and the coupler. The bore can be configured to receive the flexible shaft such that the probe retention member is slidable along the flexible shaft toward the source unit to a desired position. The coupler is configured to compress against the flexible shaft to thereby fix the probe retention member to the probe when the probe retention member is in the desired position such that a distance from a distal end of the elongate body to a distal end of the source unit is fixed.

Also disclosed is a method of calibrating an aiming device system in accordance with an embodiment. The method can comprise the steps of: attaching an intramedullary nail to an insertion handle; inserting a flexible shaft of a probe through a bore of a probe retention member along a first direction; moving the probe into a channel of the intramedullary nail until a source unit of the probe that is coupled to the flexible shaft is positioned adjacent to a distal hole of the intramedullary nail; sliding the probe retention member along the flexible shaft until the probe retention member is maintained stationary with respect to the insertion handle; and after the probe retention member is abutting the insertion handle, fixing the probe retention member to the flexible shaft.

BRIEF DESCRIPTION OF THE DRAWINGS

The foregoing summary, as well as the following detailed description of an example embodiment of the application, will be better understood when read in conjunction with the appended drawings, in which there is shown in the drawings example embodiments for the purposes of illustration. It should be understood, however, that the application is not limited to the precise arrangements and systems shown. In the drawings:

FIG. 4A is a perspective view of a probe and a probe retention member of the system shown in FIG. 3, the probe retention member being configured to be selectably fixed to the probe when in a desired position relative to the probe;

FIG. 4B is a perspective view of the probe translated within a channel defined by the intramedullary nail shown in FIG. 2A;

FIG. 4C is a sectional side elevation view of a probe positioning device constructed in accordance with an alternative embodiment;

FIG. 4D is an exploded perspective view of the probe retention member illustrated in FIG. 4A, including an actuator and a compressible member;

FIG. 5 is a perspective view of a distal alignment guide portion of the aiming device system shown in FIG. 3, the distal alignment guide portion having a pivot link, a distal aiming arm that is pivotably coupled to the pivot link, and an aiming guide that is movably and rotatably coupled to the distal aiming arm;

FIG. 6 is a perspective view of the pivot link shown in FIG. 5, the pivot link having a base that is configured to be coupled to a proximal aiming arm of the aiming device system, and an adjustable knob assembly that is configured to be coupled to the distal aiming arm such that actuating of the adjustable knob assembly causes the distal aiming arm to incrementally pivot relative to the pivot link;

FIG. 7 is a perspective view of the distal aiming arm shown in FIG. 5, the distal aiming arm defining an elongate slot;

FIG. 8A is a front perspective view of the distal aiming guide shown in FIG. 5, the distal aiming guide having a pin, a curved slot, and a pair of bone anchor guides;

FIG. 9A is a perspective view of the probe shown in FIG. 4A being inserted into the channel of the intramedullary nail such that a distal end of the probe is adjacent a distal bone anchor hole of the intramedullary nail;

FIG. 9B is a perspective view of the probe retention member shown in FIG. 4A being slid along the probe until the probe retention member abuts the insertion handle, so as to calibrate the probe;

FIG. 9C is a perspective view of the insertion handle and intramedullary nail being attached to a proximal alignment guide portion of the aiming device system;

FIG. 10 is a perspective of a distal aiming guide in accordance with another embodiment, the distal aiming guide having a pair of dynamic locking screw guides; and FIG. 11 is a perspective of a pivot link and distal aiming arm in accordance with another embodiment.

DETAILED DESCRIPTION OF ILLUSTRATIVE EMBODIMENTS

Figure 1:
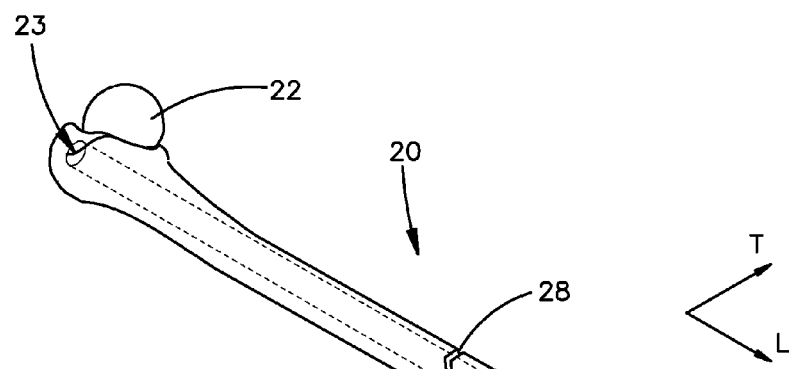
FIG. 1 is a perspective view of a humerus bone that is separated into a distal bone segment and a proximal bone segment.

Referring to FIG. 1, a long bone 20 that is elongate substantially along a longitudinal or first direction L is fractured so as to define a first or proximal bone segment 22 and a second or distal bone segment 24 that is separated from the proximal bone segment 22 at a fracture location 28. It should be appreciated that the fractured long bone 20 can define a single fracture location 28 as illustrated, or can define multiple fracture locations that separate additional bone segments from each other. While the long bone 20 is a humerus in accordance with the illustrated embodiment, the long bone 20 can be any long bone in the body that defines a medullary canal 23 (see FIG. 9E) suitable to receive an intramedullary nail 30 (See FIG. 2A) so as to fix the proximal bone segment 22 to the distal bone segment 24. For example, the long bone 20 can be a femur or a tibia.

Figure 2A:
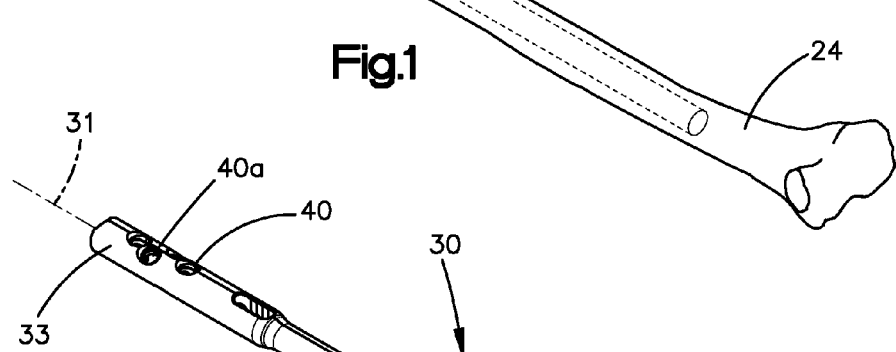
FIG. 2A is a perspective view of an embodiment of an intramedullary nail configured to affix the distal and proximal bone segments to each other, the intramedullary nail defining proximal and distal bone anchor holes.
Figure 2B:
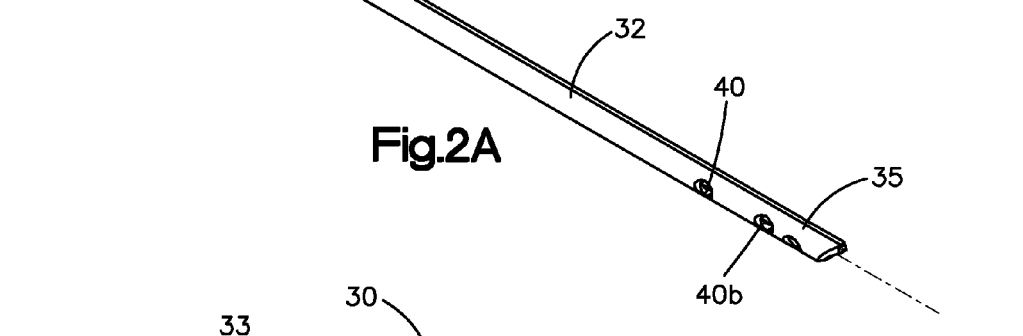
FIG. 2B is a side view of the intramedullary nail shown in FIG. 2A.

Referring now to FIGS. 2A-2B, the intramedullary nail 30 can be inserted into the medullary canal 23 of the long bone 20. The intramedullary nail 30 can include a nail body 32 that is elongate substantially along a longitudinal axis 31 that extends substantially along the longitudinal direction L. For instance, it should be appreciated that the nail body 32 can extend straight along the longitudinal direction L or can be slightly curved along the longitudinal direction L. The nail body 32 can define any suitable shape as desired, and is substantially cylindrical in cross section along a plane that is substantially perpendicular to the longitudinal axis 31 in accordance with the illustrated embodiment.

The nail body 32 defines a first or proximal portion 33 that is positioned to attach to the first or proximal bone segment 22, and an opposed second or distal portion 35 that is spaced from the first portion 33 along the longitudinal direction and positioned to attach to the second or distal bone segment 24.

The intramedullary nail 30 further defines a plurality of bone anchor holes 40 that extend into, and can further extend through, the nail body 32, for instance along a direction that is angularly offset, such as substantially perpendicular, with respect to the longitudinal axis 31. The bone anchor holes 40 can be sized to receive complementary bone anchors that are configured to secure the intramedullary nail 30 to the long bone 20. For instance, the bone anchor holes 40 can receive any suitable respective bone anchors such as nails or screws that fasten the intramedullary nail 30 to the long bone 20. At least a portion of the bone anchor holes 40 can be threaded so as to threadedly mate with complementary threaded portions of certain select ones up to all of the bone screws. Thus, the bone anchor holes 40 can be threaded, unthreaded, or threaded along a portion of their length along a transverse direction T. The bone anchor holes 40 can include at least one such as a plurality of proximal bone anchor holes 40a disposed at the proximal portion 33 of the nail body 32, and at least one such as a plurality of distal bone anchor holes 40b disposed at the distal portion 35 of the nail body 32.

Figure 3:
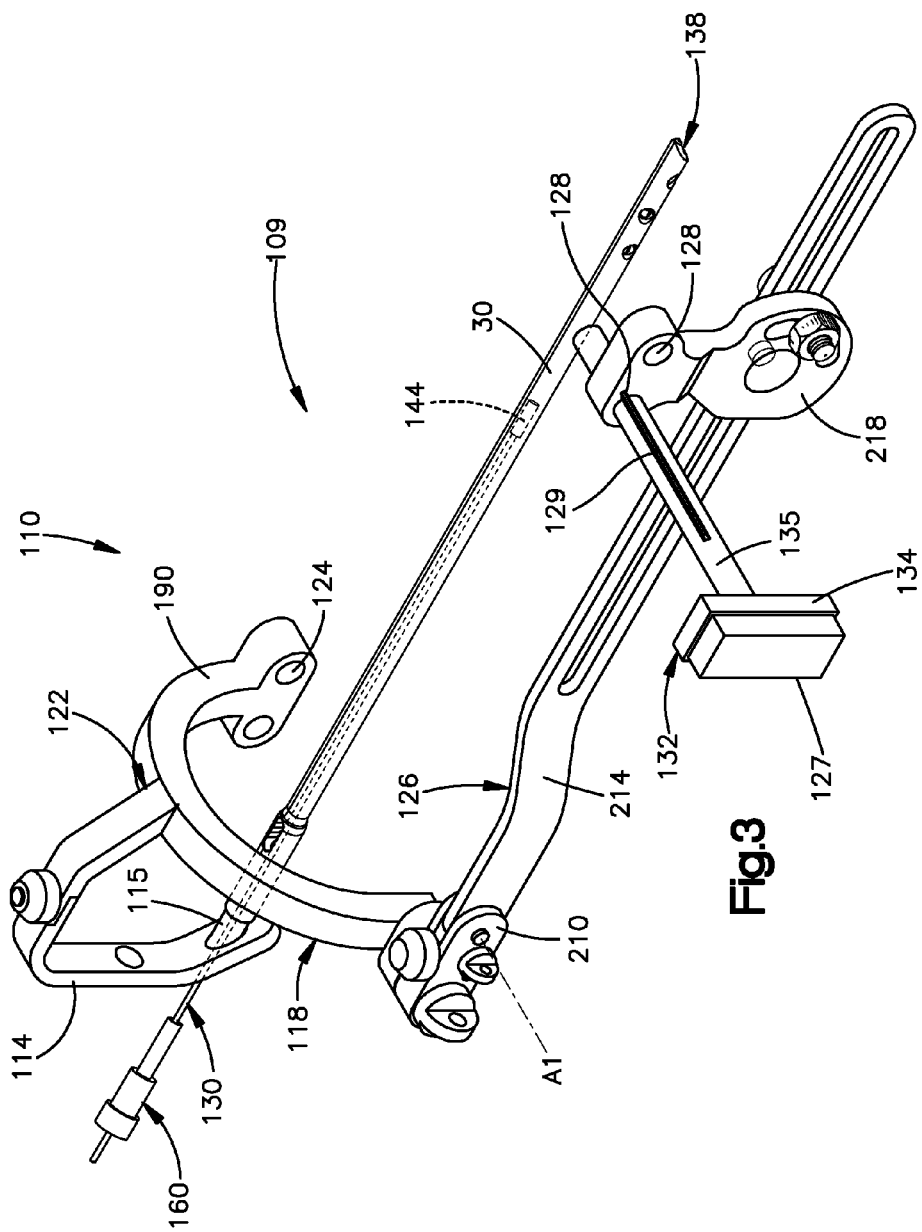
FIG. 3 is a perspective view of an intramedullary nail insertion system in accordance with an embodiment, the system including an insertion handle coupled to the intramedullary nail shown in FIG. 2A and an aiming device system that is coupled to the insertion handle.

Now referring to FIG. 3, an intramedullary nail system 109 that includes the nail 30 and an intramedullary nail insertion system 110. The intramedullary nail insertion system 110 is configured to be coupled to the intramedullary nail 30 and is further configured to insert the nail 30 into the medullary canal 23 of the long bone 20. The insertion system 110 includes an insertion handle 114 configured to be coupled to the intramedullary nail 30 and an aiming device system 118 that is configured to be coupled to the insertion handle 114. For instance, the handle can support an intramedullary nail support member 115 that, in turn, is coupled to the intramedullary nail. In one example, the intramedullary nail support member 115 can be configured to be threaded into the proximal portion 33 (see FIG. 2A) of the intramedullary nail 30. Thus, the intramedullary nail support member 115 can be referred to as a connection screw. The aiming device system 118 is configured to align bone anchor guides with the bone anchor holes 40 of the intramedullary nail 30. In particular, the aiming device system 118 includes a proximal alignment guide portion 122 having at least one proximal bone anchor guide 124 that is configured to guide a bone anchor to a respective proximal bone anchor hole 40a of the intramedullary nail 30 and a distal alignment guide portion 126 having at least one distal bone anchor guide 128 that is configured to guide a bone anchor to a respective distal bone anchor hole 40b of the intramedullary nail 30. In the illustrated embodiment, the proximal alignment guide portion 122 has two proximal bone anchor guides 124 and the distal alignment guide portion 126 has two distal bone anchor guides 128. It should be appreciated, however, that the proximal and distal alignment guide portions 122 and 126 can have any number of bone anchor guides 124 and 128 as desired.

Figure 9D:
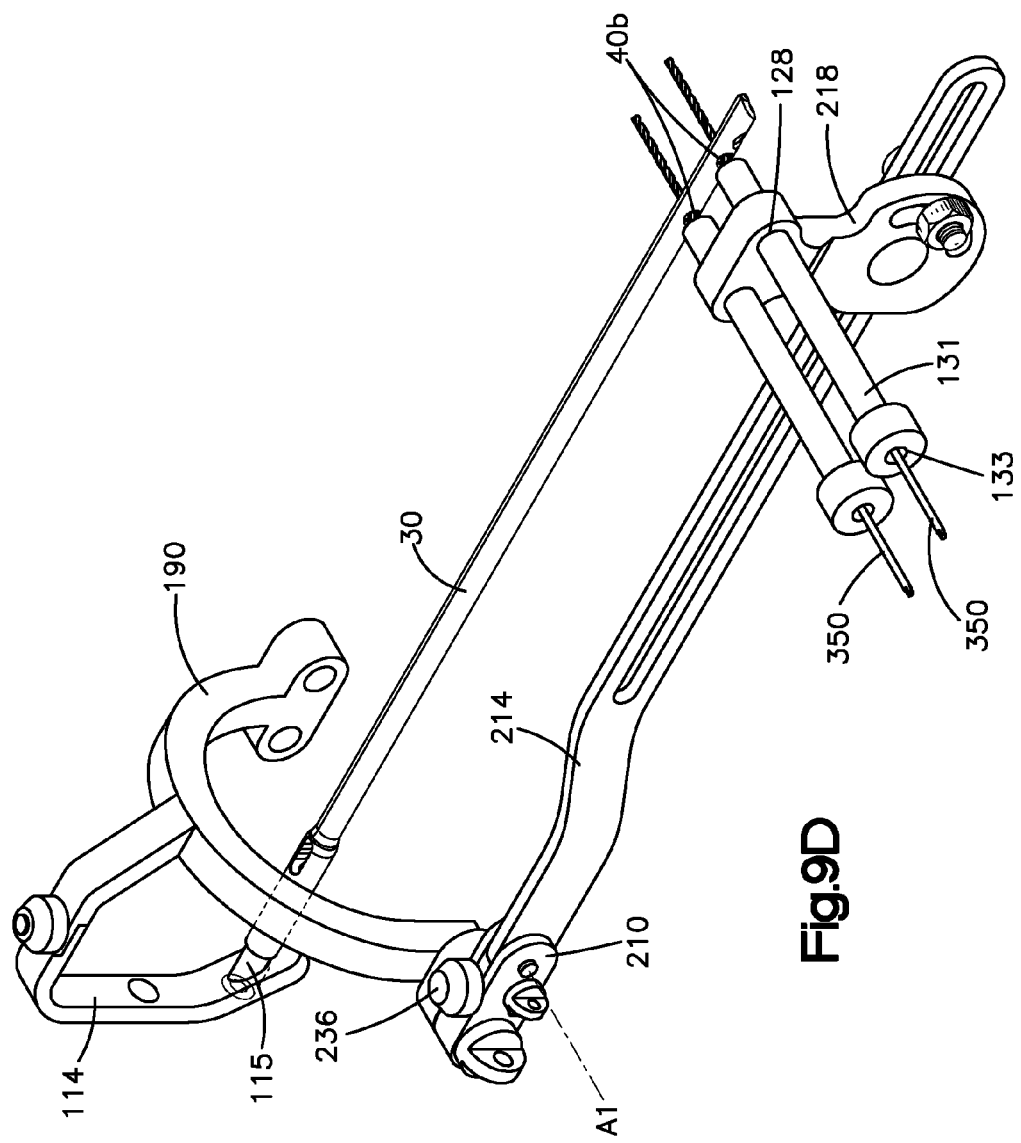
FIG. 9D is a perspective view of the distal alignment guide portion attached to the proximal alignment guide portion such that the distal bone anchor guides of the distal aiming guide are aligned with the distal bone anchor holes of the intramedullary nail.

The bone anchor guides 124 and 128 are configured as bores that are configured to retain respective sleeves, for example sleeves 131 shown in FIG. 9D. Each sleeve 131 is elongate and is configured to guide a respective bone anchor toward and into a respective bone anchor hole 40 of the intramedullary nail 30. In particular each sleeve defines a channel 133 that extends toward the respective bone anchor hole 40 such that the channel 133 receives the bone anchor and guides it toward the bone anchor hole 40. It should be appreciated, however, that the bone anchor guides 124 and 128 can have other configurations as desired. For example, the bone anchor guides 124 and 128 can be configured as C-clips that receive the sleeves 131, as desired.

With continued reference to FIG. 3, the aiming device system 118 is to be coupled to the intramedullary nail 30 (e.g. via the insertion handle 114) such that the bone anchor guides 124 and 128 are substantially aligned with the proximal and distal bone anchor holes 40a and 40b of the intramedullary nail 30 (i.e. a central axis of each guide 124 and 128 is coaxial with a central axis of a respective bone anchor hole 40a and 40b) so that a drill and/or bone anchors may be guided into the bone anchor holes 40a and 40b. Upon insertion of the intramedullary nail 30 into the medullary canal 23, however, the intramedullary nail 30 may deform such that the central axes of the distal bone anchor guides 128 are no longer aligned with the central axes of the distal bone anchor holes 40b.

To realign the distal bone anchor guides 128 and the distal bone anchor holes 40b, the aiming device system 118 can include a probe 130 and a position sensor assembly 132, which includes a position sensor unit 134 that is configured to communicate with the probe 130 to provide an indication when the distal bone anchor guides 128 are aligned with the distal bone anchor holes 40b for example as described in United States Publication No. 2013/0018381 the contents of which are hereby incorporated by reference as if set forth in their entirety herein. The probe 130 is configured to be inserted into a longitudinal channel 138 of the intramedullary nail 30 and the sensor unit 134 can be coupled to the distal alignment guide portion 126. As will be described, the distal alignment guide portion 126 can be adjusted to bring the probe 130 and sensor unit 134 in alignment. When the sensor unit 134 indicates that it is aligned with the probe 130, the distal bone anchor guides 128 will be aligned with the distal bone anchor holes 40b.

As shown in FIG. 4A, the probe 130 is elongate along the longitudinal or first direction L and defines a distal end $D_P$ and a proximal end $P_P$ that is spaced from the distal end along the first direction L. The probe 130 includes a flexible shaft 140 that is elongate along the first direction and a source unit 144 coupled to the distal end of the flexible shaft 140. The source unit 144 is sized such that the source unit 144 is translatable within the longitudinal channel 138 of the intramedullary nail 30. The source unit 144 is configured to emit a position signal that is received by the position sensor unit 134. For example, the source unit 144 can be a magnet that emits a magnetic field. It should be appreciated, however, that the source unit 144 can have other configurations as desired.

Referring also to FIG. 3, the position sensor assembly 132 can include the position sensor unit 134, a base 135 that supports the position sensor unit 132, and the indicator 127 supported by the position sensing unit 132. The base 135 can be transparent, translucent, or configured as desired. The base 135 can include a key that engages the bone anchor guide 128 so as to orient the position sensor assembly in a desired orientation when the base 135 is inserted in the bone anchor guide 128. For instance, the base 135 can include an outwardly projecting rib 129 that is configured to be inserted into a complementary slot in the respective bone anchor guide 128 so as to orient the position sensor assembly in a desired orientation. It should be appreciated that the key can be configured in accordance with any suitable embodiment. For instance, the key can alternatively be configured as a recess into the base 135. The sensor unit 134 is configured to detect a signal such as a magnetic field generated by the magnet 144. The sensor unit 134 is configured to be coupled to the distal alignment guide portion 126, such as to one of the distal bone anchor guides 128, and the display 127, such as an LED color indicator, (see FIG. 3) is configured to indicate when the sensor unit 134 and source unit 144 are aligned and/or misaligned. For example, the light can be red when the sensor and source units 134 and 144 are misaligned and green when the sensor and source units 134 and 144 are aligned. If the sensor unit 134 and source unit 144 are misaligned, adjustment of the distal alignment guide portion 126 can bring the sensor unit 134 into alignment with the source unit 144.

To ensure that the probe 130 or at least the source unit 144 is in the correct position within the channel 138 of the intramedullary nail 30, the aiming device system 118 can further include a probe retention member 160 that is configured to slide along the flexible shaft 140 of the probe 130 and subsequently be fixed to the flexible shaft 140 when in the desired position. As shown in FIG. 4A, the probe retention member 160 includes an elongate body 164 and a coupler 168 attached to the elongate body 164. The probe retention member 160 further defines a bore 172 that extends through both the elongate body 164 and the coupler 168. The bore 172 is configured to receive the flexible shaft 140 such that the probe retention member 160 is slidable along the shaft 140 toward and away from the source unit 144. As shown in FIG. 4A, the elongate body 164 can be cylindrical and can include a shoulder 178 proximate to its proximal end. The shoulder 178 is configured to abut the nail support member 115 to thereby provide an insertion stop for the probe 130. It should be appreciated that the connection member 115 is supported by the insertion handle 114. Accordingly, it can be said that when the shoulder 178 abuts the nail support member 115, the shoulder 178 also abuts the insertion handle 114, albeit indirectly. Alternatively, the intramedullary nail insertion system 110 can alternatively be configured such that the shoulder 178 abuts the insertion handle direction 114 as desired. Thus, it should be appreciated that the probe retention member 160 and the probe 130 are maintained stationary with respect to the handle 114. It should be appreciated, however, that the elongate body 164 can have any shape as desired and that any portion of the elongate body 164 can be configured to abut the insertion handle 114 as desired.

The coupler 168 is configured to selectably fix the probe retention member 160 to the flexible shaft 140. For example, the coupler 168 can be configured to compress against the flexible shaft 140 to thereby fix the probe retention member 160 to the flexible shaft 140 when the probe retention member 160 is in the desired position. As shown in FIG. 4A, the coupler 168 can include an actuator and a compressible portion 185 that is configured to be coupled to the actuator such that the actuator can cause the compressible portion 185 to compress against the flexible shaft 140 to thereby fix the probe retention member to the flexible shaft 140. In one example, the actuator can be configured as a rotatable knob 182, such that rotation of the rotatable knob 182 about the flexible shaft 140 causes the compressible portion 185 to compress against the flexible shaft 140 to thereby fix the probe retention member 160 to the flexible shaft 140 similar a drill chuck. It should be appreciated, however, that the coupler 168 can have other configurations as desired. For example, the coupler 168 can be configured as a tab or a set screw that compresses against the shaft 140 as desired.

In operation, the probe 130 is translated into the channel 138 of the intramedullary nail 30 while the nail is attached to the insertion handle 114. The probe 130 is translated until the source unit 144 is adjacent a first distal bone anchor hole 40b of the intramedullary nail 30 as shown in FIG. 4B. For instance, the user can visually confirm by visual inspection of the distal bone anchor hole 40b to confirm whether the source unit 144 has reached its desired position immediately proximal with respect to the distal bone anchor hole 40b. Alternatively, as illustrated in FIG. 4C, the intramedullary nail insertion system 110 can include a probe positioning device 137 having a head 139, and a shaft 141 that extends from the head 139. The shaft 141 is sized to be inserted within the channel 138 of the intramedullary nail 30 at the distal portion 35. The head 139 is sized greater than the channel 138 so as to define a stop surface 139a that abuts the distal end of the intramedullary nail 30. The shaft 141 defines a distal end 141a that is spaced from the stop surface 139a a predetermined distance equal to the distance from the distal end of the intramedullary nail 30 to a position immediately proximal with respect to a select one of the distal bone anchor holes 40b. Thus, during operation, the shaft 141 can be inserted until the stop surface 139 abuts the distal end of the intramedullary nail 30, and the probe 130 can be translated in the longitudinal channel 138 of the intramedullary nail 30 along the distal direction until the source unit 144 abuts the distal end 414a of the shaft 141. Alternatively still, the intramedullary nail insertion system 110 can include a probe positioning device that is sized to be inserted into the select distal bone anchor hole 40b, and the probe 130 can be translated in the longitudinal channel 138 of the intramedullary nail 30 along the distal direction until the source unit 144 abuts the probe positioning device.

Once the probe 130 is in the desired position, the proximal end of the flexible shaft 140 is inserted into the bore 172 of the probe retention member 160 and the probe retention member 160 is translated along the flexible shaft 140 and positionally fixed with respect to the handle 114. For instance, as illustrated in FIGS. 3-4B, the probe retention member 160 can be translated along the flexible shaft 140 in the distal direction until the shoulder 178 abuts the nail support member 115 as described above. Next, the coupler 168 can be fixed to the flexible shaft 140. In one example, the knob 182 can be rotated to thereby cause the compressible portion 185 of the coupler 168 to compress against the flexible shaft 140 and fix the probe retention member 160 to the shaft 140. As illustrated in FIG. 4D, the compressible portion 185 can include a plurality of compressible sections 185a that are spaced apart and cooperate to define a channel 185b that extends through the compressible portion 185 and is sized to receive the flexible shaft. The sections 185a can be threaded and configured to threadedly mate with the knob 182. As the knob 182 is threadedly advanced onto the compressible portion 185, the sections 185a compress against each other, thereby narrowing the channel 185b, and tightening the sections 185a against the flexible shaft 140 that extends through the channel 185b.

Figure 4E:
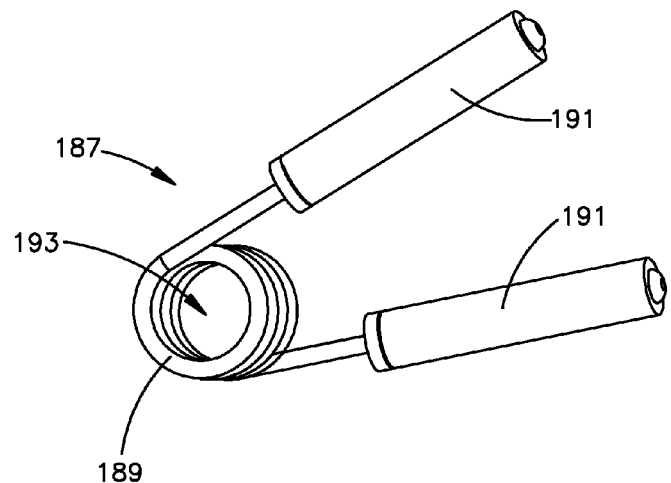
FIG. 4E is a perspective view of an actuator configured for use with the compressible member illustrated in FIG. 4D, but constructed in accordance with an alternative embodiment.

Alternatively, as illustrated in FIG. 4E, the actuator can be configured as a spring clip 187 having a coil spring 189 and a pair of grips 191 attached to opposed ends of the coil spring 189. The spring clip 187 defines a channel 193 that extends through the coil spring 189. When the coil spring 189 is in a relaxed position, the channel 193 is sized such that the coil spring 189 is tightened about the compressible member 185, thereby causing the flexible member 185 to be positionally fixed to the flexible shaft 140 in the manner described above with respect to FIG. 4D. When the grips 191 are compressed toward each other, the coil spring 189 increases the size of the channel 193, such that the coil spring 189 is movable over the compressible member 185, thereby inserting the compressible member 185 in the channel 193. Thus, during operation, the grips 191 are compressed toward each other, the coil spring 189 is brought over the compressible member 185 so as to insert the compressible member 185 in the channel 193, and the grips 191 are subsequently released, thereby causing the coil spring 189 to apply a force against the compressible member 185 that causes the compressible member 185 to compress against the flexible shaft 140.

The probe retention member 160 further defines a bore 172 that extends through both the elongate body 164 and the coupler 168. The bore 172 is configured to receive the flexible shaft 140 such that the probe retention member 160 is slidable along the shaft 140 toward and away from the source unit 144. As shown in FIG. 4A, the elongate body 164 can be cylindrical and can include a shoulder 178 proximate to its proximal end. The shoulder 178 is configured to abut the nail support member 115 to thereby provide an insertion stop for the probe 130. It should be appreciated that the nail support member 115 is supported by the insertion handle 114. Accordingly, it can be said that when the shoulder 178 abuts the nail support member 115, the shoulder 178 also abuts the insertion handle 114, albeit indirectly. Alternatively, the intramedullary nail insertion system 110 can alternatively be configured such that the shoulder 178 abuts the insertion handle direction 114 as desired. Thus, it should be appreciated that the probe retention member 160 and the probe 130 are maintained stationary with respect to the handle 114. It should be appreciated, however, that the elongate body 164 can have any shape as desired and that any portion of the elongate body 164 can be configured to abut the insertion handle 114 as desired.

Figure 4F:
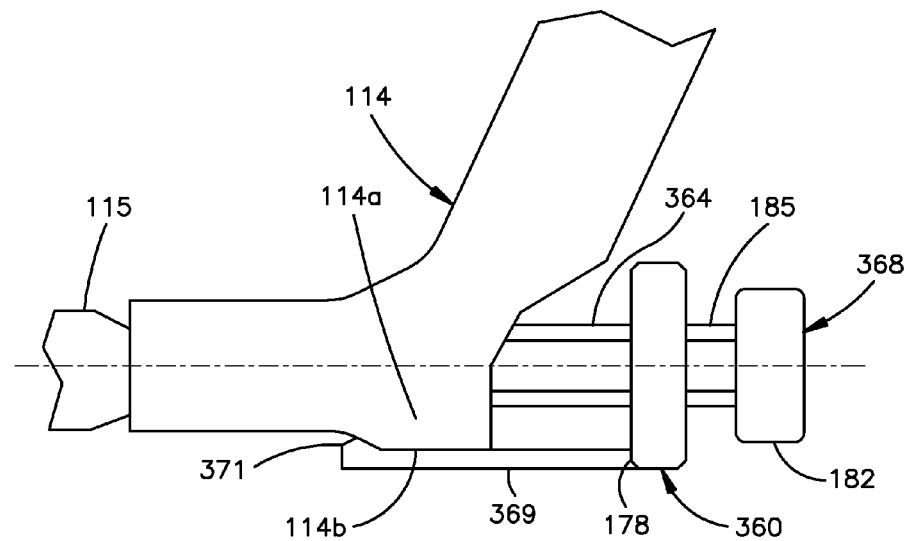
FIG. 4F is a side elevation view of a coupler constructed in accordance with an alternative embodiment.

Alternatively, as illustrated in FIG. 4F, a probe retention member 360 constructed in accordance with another embodiment can include an elongate body 364 and a coupler 368 attached to the elongate body 364. The coupler can include an actuator, such as the knob 182 described above. Alternatively, the actuator can be configured as the spring clip 187 described above. Alternatively still, the actuator can be constructed in accordance with any embodiment suitable to compress the compressible member 185 against the flexible shaft 140. The probe retention member 360 can include a flexible snap arm 369 that extends in the distal direction from the shoulder 178, and is cantilevered from the shoulder 178. The snap arm 369 is spaced from the elongate body 364 a distance so as to define a gap that is sized to receive an annular portion 114a of the handle 114 when the body 364 is inserted into the nail support member 115, and thus into the handle 114. The annular portion 114a of the handle 114 includes an external engagement surface 114b. The snap arm 369 can include a projection 371 that faces the elongate body 364. The distance between the projection 371 and the elongate body 364 is less than the thickness of the annular portion 114a of the handle 114 when the snap arm 369 is in a relaxed position. As the elongate body 364 is advanced within the nail support member 115, the projection 371 cams over the engagement surface 114b of the handle 114, thereby resiliently deflecting the snap arm 369 away from the elongate body 364. Once the projection 371 has moved distally from the engagement surface of the handle, the snap arm 369 moves toward the elongate body 364, thereby capturing the annular portion 114a of the handle between the snap arm 369 and the elongate body 364. While probe retention members have been describe in accordance with various embodiments, it should be appreciated that any suitable probe retention member configured to be fixed to the flexible shaft 140 and independently positionally fixed with respect to the handle 114 is contemplated.

When the probe retention member 160 is positionally fixed with respect to the the shaft 140, a distance measured from a distal end of the elongate body 164 to a distal end of the source unit 144 is fixed, thereby calibrating the probe 130. Therefore, when the probe 130 is subsequently removed from the channel 138 while the probe retention member 160 is fixed to the flexible shaft 140, the probe 130 can be reinserted into the channel 138 after the intramedullary nail 30 has been moved into the medullary canal 23, and the probe retention member can be again fixed with respect to the shaft 140. Accordingly, the source unit 144 is repositioned in the desired position adjacent the first distal bone anchor hole 40b of the intramedullary nail 30. That is, the probe 130 can be reinserted into the channel 138 and moved along the channel 138 until the shoulder 178 abuts the intramedullary nail support member 115 as described above, or until the snap arm 369 attaches to the handle, as described above with respect to FIG. 4F. When the probe is positionally fixed with respect to the handle 114, the source unit 144 will be correctly positioned (e.g. adjacent the first distal bone anchor hole 40b). In this way, the probe 130 and probe retention member 160 can be referred to as a probe calibration system.

Referring now to FIGS. 3 and 5, the aiming device system 118 and in particular the distal alignment guide portion 126 is configured to be adjusted so as to align at least one of the distal bone anchor guides 128 to a first distal bone anchor hole 40b of the intramedullary nail 30. As shown in FIG. 3, the distal alignment guide portion 126 is coupled to a proximal aiming arm 190 of the proximal alignment guide portion 122. In the illustrated embodiment, the distal alignment guide portion 126 includes a pivot link 210, a distal aiming arm 214 that is pivotably coupled to the pivot link 210 such that the distal aiming arm 214 is pivotable relative to the pivot link about an arm axis $A_1$, and an aiming guide 218 that is configured to be coupled to the distal aiming arm 214. The aiming guide 218 carries the two distal bone anchor guides 128 and is configured to be translated along the distal aiming arm 214, and can alternatively or additionally be rotatable relative to the distal aiming arm 214 to thereby at least partially align the distal bone anchor guides 128 with respective ones of the distal bone anchor holes 40b of the intramedullary nail 30.

As shown in FIG. 6, the pivot link 210 includes base member 228, a fixation element 232 configured to couple the base member to the proximal aiming arm 190, and an adjustment knob assembly 236 that is configured to mate with the distal aiming arm 214 such that actuation of the adjustment knob assembly 236 causes the distal aiming arm 214 to incrementally pivot about the arm axis $A_1$.

With continued reference to FIG. 6, the base member 228 can be elongate along the first direction L and can include a pair of plates 238 that are spaced from each other along the transverse direction T so as to define an arm receiving channel 239 that is configured to receive a proximal end of the distal aiming arm 214 such that the distal aiming arm 214 is pivotable about the arm axis $A_1$. As shown, the base member 228 defines a slot 244 that is elongate along the first direction L and is open to the arm receiving channel 239. In the illustrated embodiment the slot 244 is offset proximally from the arm axis $A_1$ though it should be appreciated, that the slot 244 can be distal to the arm axis $A_1$ as desired. The base member 228 can further define an aperture 248 that extends therethrough along the transverse direction T and is configured to receive the fixation element 232 to thereby fix the pivot link 210 to the proximal aiming arm 190. In the illustrated embodiment, the fixation element 232 is configured as a snap pin and can be inserted through the aperture 248 and into the proximal aiming arm 190 to thereby fix the pivot link 210 to the proximal aiming arm 190. It should be appreciated, however, that the pivot link 210 can be fixed to the proximal aiming arm 190 using any structure as desired.

With continued reference to FIG. 6, the adjustment knob assembly 236 includes a threaded shaft 250 and a grip 256 coupled to the threaded shaft 250. The threaded shaft 250 extends into the arm receiving channel 239 along a lateral direction A and through a threaded bore 282 of the aiming arm 214. The threads of the shaft 250 can threadedly mate with the distal aiming arm 214 in the threaded bore 282, such that rotation of the grip 256 with respect to the distal aiming arm 214 causes the distal aiming arm 214 to pivot about the arm axis $A_1$. For instance, clockwise rotation of the grip 256 can cause the distal aiming arm 241 to pivot in a first direction about the arm axis $A_1$, and counterclockwise rotation of the grip 256 can cause the distal aiming arm 241 to pivot in a second direction opposite the first direction about the arm axis $A_1$. As shown in FIG. 6, the adjustment knob assembly 236 further includes a holding pin 260 that extends through the elongate slot 244 and couples to the threaded shaft 250 to thereby attach the adjustment knob assembly 236 to the pivot link 210. The elongate slot 244 allows the holding pin 260 to move within the slot 244 as the distal aiming arm 214 is pivoted about the arm axis $A_1$. It should be appreciated, however, that the adjustment knob assembly 236 can have other configurations as desired. For example, the threaded shaft can include a ball that mates with a socket joint defined by the distal aiming arm 214, as desired.

In particular, referring now to FIGS. 5-7, the distal aiming arm 214 is pivotably coupled to the plates 238 of the pivot link 210 by a pin 270. The pin 270 defines the arm axis $A_1$ and is positioned distal to the adjustment knob assembly 236. As shown, the distal aiming arm 214 is elongate along the first direction L and includes a sliding support 274 that is configured as a slot 278 that is also elongate along the first direction L. As described above, the distal aiming arm 214 further includes the threaded bore 282 proximal to the sliding support 274 and to the arm axis $A_1$. The threaded bore 282 extends into the arm receiving channel 239 and is configured to receive the threaded shaft 250 of the adjustment knob assembly 236 such that rotation of the knob assembly causes the aiming arm 214 to incrementally pivot about the arm axis $A_1$. As shown in FIG. 5, the sliding support 274 is configured to support the aiming guide 218 such that the aiming guide 218 is selectably translatable along the sliding support 274 and is also selectably rotatable relative to the aiming arm 214 about a guide body axis $A_2$ that extends along the transverse direction T. It should be appreciated, however, that the sliding support 274 can have other configurations as desired. For example, while the sliding support can be configured as an elongate slot, the sliding support can alternatively be configured as a rail or other suitable structure as desired.

Figure 8B:
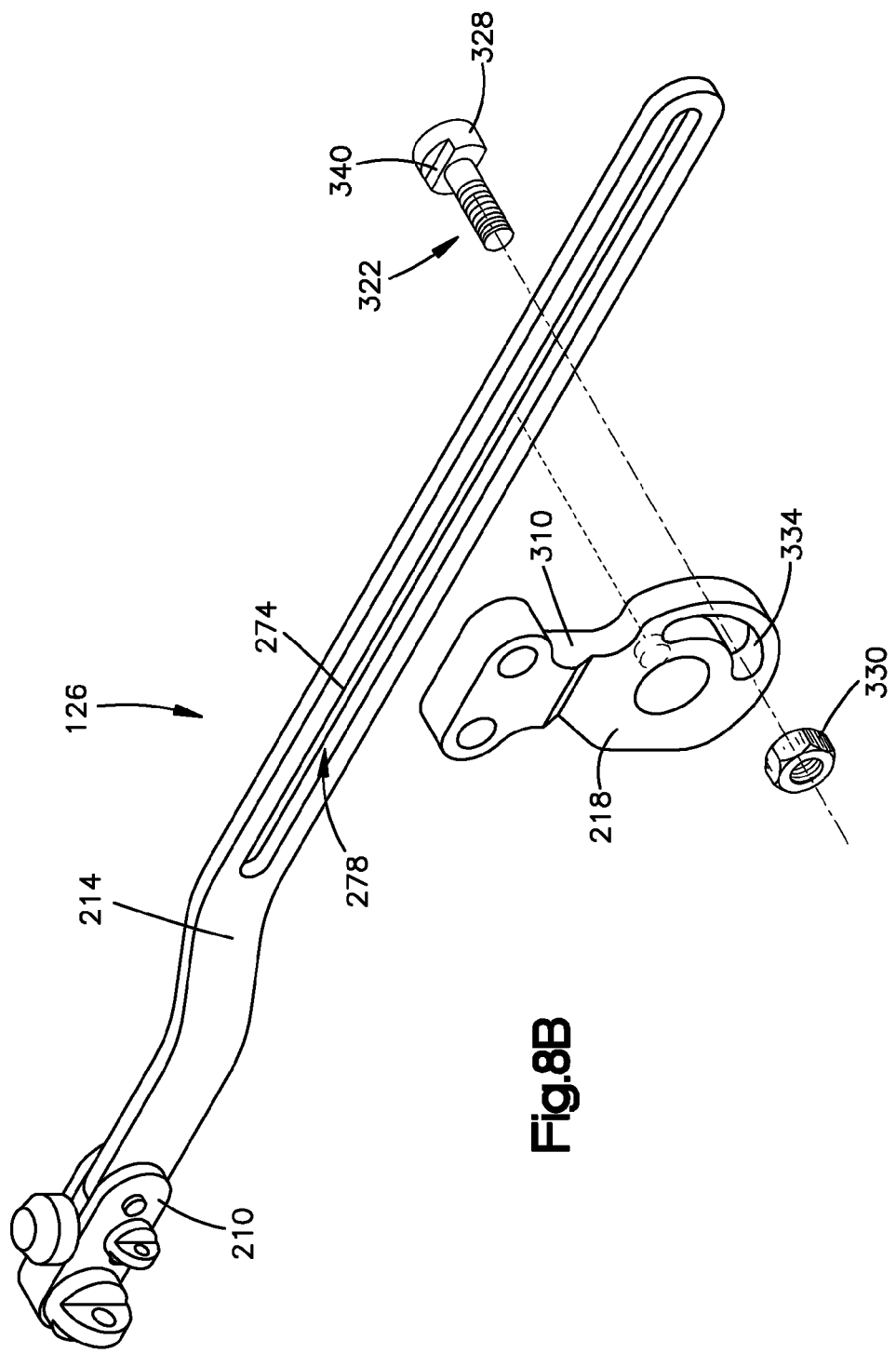
FIG. 8B is a perspective view of the distal aiming guide shown in FIG. 8A being attached to the distal aiming arm shown in FIG. 7.

Now in reference to FIGS. 5 and 8A-8B, the aiming guide 218 includes a guide body 310 that defines the at least a first distal bone anchor guide 128 that is configured to retain a first guide sleeve 131. In the illustrated embodiment, the guide body 310 defines a first and second distal bone anchor guide 128 that are each configured to retain a respective guide sleeve 131. At least one of the first and second distal bone anchor guides 128, such as the second distal bone anchor guide 128 is also configured to retain the sensor unit 134 prior to the second bone anchor guide 128 retaining the second guide sleeve 131 so that the distal bone anchor guides 128 can be aligned with the distal bone anchor holes 40b of the intramedullary nail 30 using the sensor unit 134 and probe 130 as described above. For example, alignment of the sensor unit 134 and magnet 144 aligns the first distal bone anchor guide 128 and thus the guide sleeve 131 that is retained by the first distal bone anchor guide 128 with the first distal bone anchor hole 40b of the intramedullary nail 30. As a result, when the aligned sensor unit 134 is replaced with the second guide sleeve 131, the second guide sleeve 131 will be aligned with the second distal bone anchor hole 40b of the intramedullary nail 30.

As shown in FIGS. 8A and 8B, the aiming guide 218 can further include an attachment mechanism 322 that is configured to mate with the sliding support 274 to thereby attach the guide body 310 to the aiming arm 214 such that the guide body 310 is both selectably movable along the sliding support 274 along the first direction L, and selectably rotatable relative to the aiming arm 214 about the guide body axis $A_2$. As shown in FIGS. 8A and 8B, the aiming guide 218 includes a pin 326 that extends out from the guide body 310 such that the pin 326 defines the guide body axis $A_2$. The first and second guide attachment members 328 and 330 are configured to be secured to each other so as to fix the guide body 310 to the aiming arm 214. For example, the pin 326 can be configured to be inserted through the slot 278 of the aiming arm 214 such that the pin 326 is slidable within the slot 278. When the guide body 310 has been rotated about the guide body axis $A_2$ to a desired rotational position and slid along the slot 278 to a desired longitudinal position, the first and second guide attachment members 328 and 330 can be tightened to thereby fix the guide body 310 to the aiming arm 214 in the desired orientation.

With continued reference to FIGS. 8A and 8B, the aiming guide 218 further defines a curved or arcuate slot 334 that extends through the guide body 310 along the transverse direction T. The slot 334 is curved, and the pin 326 can extend through the slot 334 in an initial position within the curve, for instance at a substantial center of the curve. The first aiming guide attachment member 328 is configured to extend through the slot 278 of the aiming arm 214 and through the curved slot 334 of the guide body 310. The second aiming guide attachment member 330 is configured to mate with the first aiming guide attachment member 328 to thereby attach the guide body 310 to the aiming arm 214. When the second aiming guide attachment member 330 is further tightened to the first aiming guide attachment member 328 the guide body 310 will be compressed against the aiming arm 214 and thus fixed to the aiming arm 214. In the illustrated embodiment, the first aiming guide attachment member is configured as a screw that defines a flattened surface 340 and the second aiming guide attachment member 330 is a knob that threadedly receives the screw such that rotation of the knob about the screw in a first rotational direction fixes the position of the guide body 310 relative to the aiming arm 214 and rotation of the knob in a second rotational direction that is opposite the first rotational direction loosens the screw so as to allow the guide body 310 to move relative to the aiming arm 214. The flattened surface 340 is received into the slot 278 of the aiming arm 214 and abuts the aiming arm 214 such that the screw is rotatably fixed relative to the aiming arm 214 when the screw is received by the slot 278. Therefore when the first and second guide attachment members 328 and 330 are loosened the guide body 310 can be translated along the aiming arm such that the pin 326 moves within in the slot 278 and can also be rotated relative to the aiming arm 214. As the guide body 310 is rotated the first guide attachment member 328 will move within the curved slot 334, thereby causing the aiming guide 218 to rotate about the guide body axis $A_2$. Once the guide body 310 is in the desired rotational and translational position, the first and second guide attachment members 328 and 330 can be tightened to thereby fix the guide body 310 in the desired position.

With continued reference to FIG. 8A, the aiming guide 218 can further include a pair of stops 344 that extend out from the guide body 310 on respective sides of the pin 326. The stops 344 are configured to be disposed on opposed sides of the aiming arm 214 when the pin 326 is received within the slot 278. The stops 344 can be spaced from each other such that as the guide body 310 rotates about the axis $A_2$ the stops 344 will eventually contact the aiming arm 214 thereby preventing further rotation relative to the aiming arm 214. The stops 334 further provide a visual indication that the aiming guide 218 has been correctly assembled such that the distal aiming arm 214 is positioned between the stops 334.

Now in reference to FIGS. 9A-9I, the aiming device system can be calibrated prior to the intramedullary nail 30 being inserted into the medullary canal of a bone 20. As shown in FIG. 9A, the intramedullary nail 30 can be fixed to the insertion handle 114 and the probe 130 can be translated into the channel 138 of the intramedullary nail 30. The probe 130 is translated until the source unit 144 is adjacent a first distal bone anchor hole 40b of the intramedullary nail 30 as shown in FIG. 9A. Once in position, the proximal end of the flexible shaft 140 is inserted into the bore 172 of the probe retention member 160 and the probe retention member 160 is slid along the flexible shaft 140 until the shoulder 178 abuts the intramedullary nail support member 115 as shown in FIG. 9B. When the shoulder 178 is in abutment with the intramedullary nail support member 115, the probe retention member 160 can be fixed to the shaft 140 in accordance with any suitable embodiment as desired. When the probe retention member 160 is fixed to the shaft 140, a distance measured from a distal end of the elongate body 164 to a distal end of the source unit 144 is fixed, thereby calibrating the probe 130 to be in alignment with the respective one of the distal bone anchor holes 40b.

As shown in FIG. 9C, the probe 130 with the probe retention member 160 fixed to the shaft 140 is removed from the channel 138 and the insertion handle 114 can be attached to proximal aiming arm 190. As shown in FIG. 9D the distal aiming arm 214 can be fixed to the proximal aiming arm 190 via the pivot link 210 as described above. The distal aiming arm 214 and the aiming guide 218 can be adjusted such that the distal bone anchor guides 128 are aligned with the distal bone anchor holes 40b of the intramedullary nail 30. For example, the distal aiming arm 214 can be pivoted about the arm axis $A_1$ by actuating the adjustment knob assembly 236 and the aiming guide 218 can be adjusted by moving it along the distal aiming arm 214 and/or by rotating it relative to the distal aiming arm 214. Once in position drill bits 350 can be inserted through the sleeves 131 and into the distal bone anchor holes 40b to confirm that the distal bone anchor guides 128 are aligned with the distal bone anchor holes 40b. At this time the distal alignment guide portion 126 and the probe 130 are calibrated for the procedure.

Figure 9E:
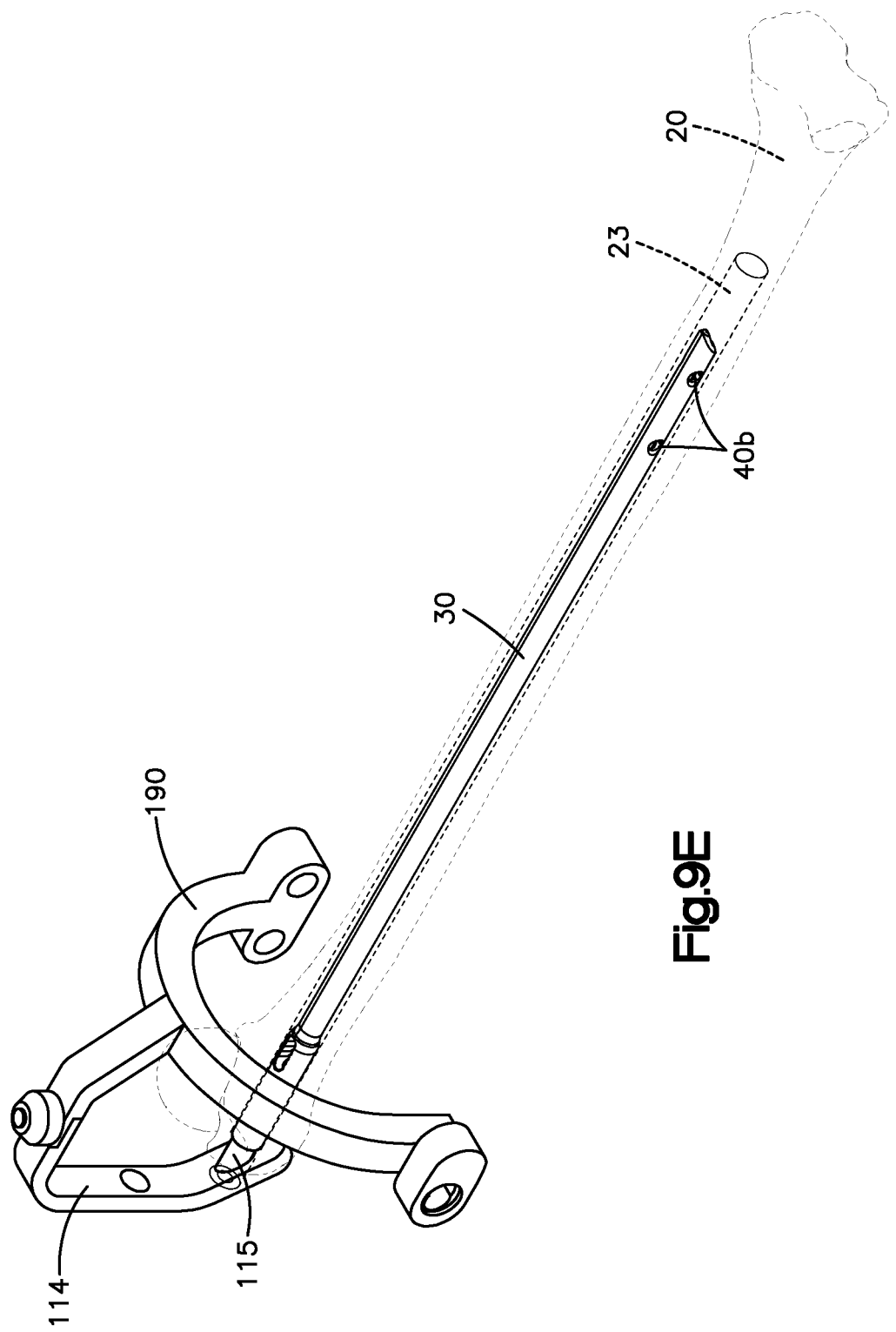
FIG. 9E is a perspective view of the intramedullary nail being inserted into the medullary canal of the humerus bone.
Figure 9F:
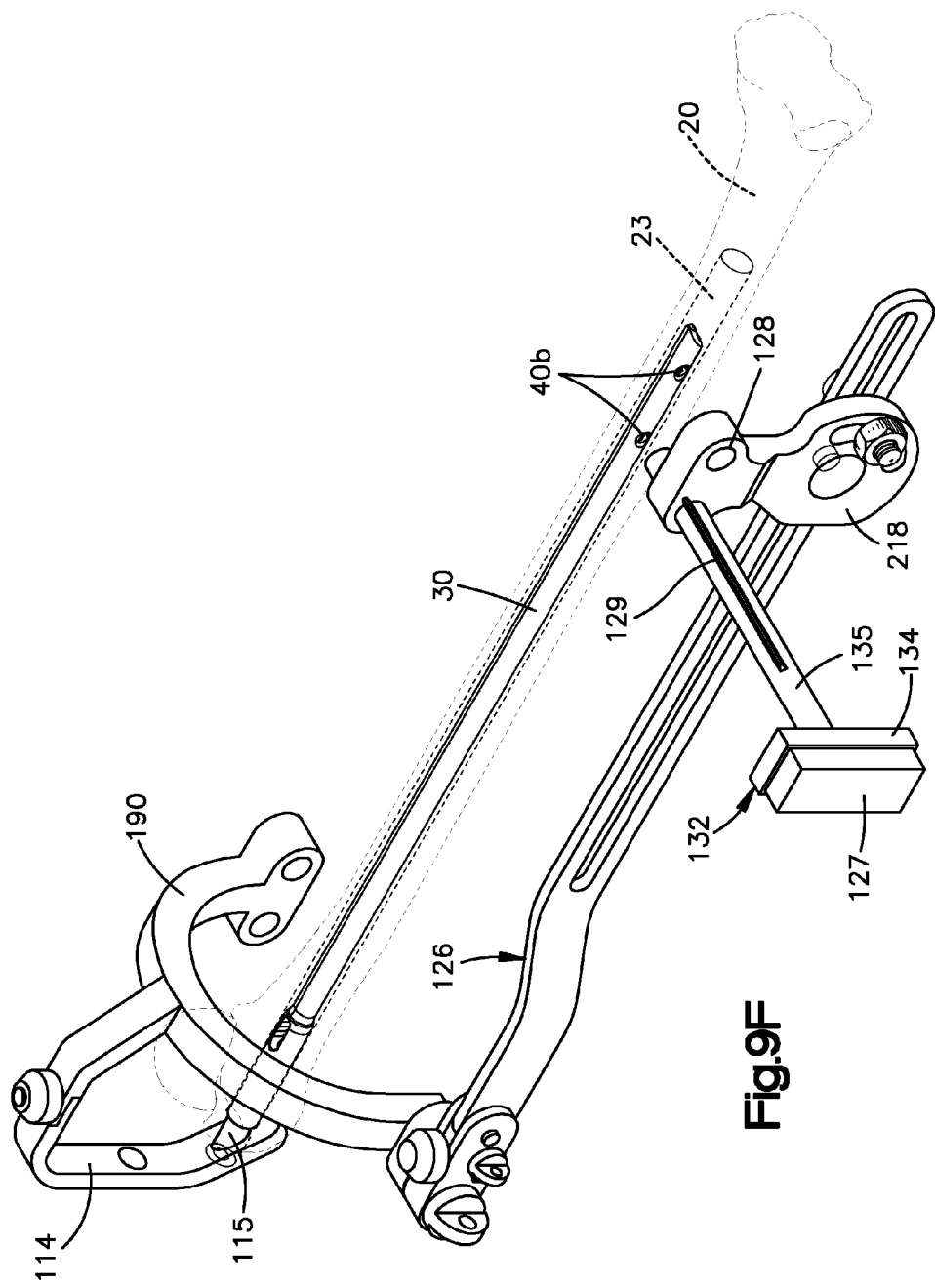
FIG. 9F is a perspective view of the distal alignment guide portion attached to the proximal alignment guide portion with a sensor unit coupled to the distal aiming guide after the nail has been inserted into medullary canal.
Figure 9G:
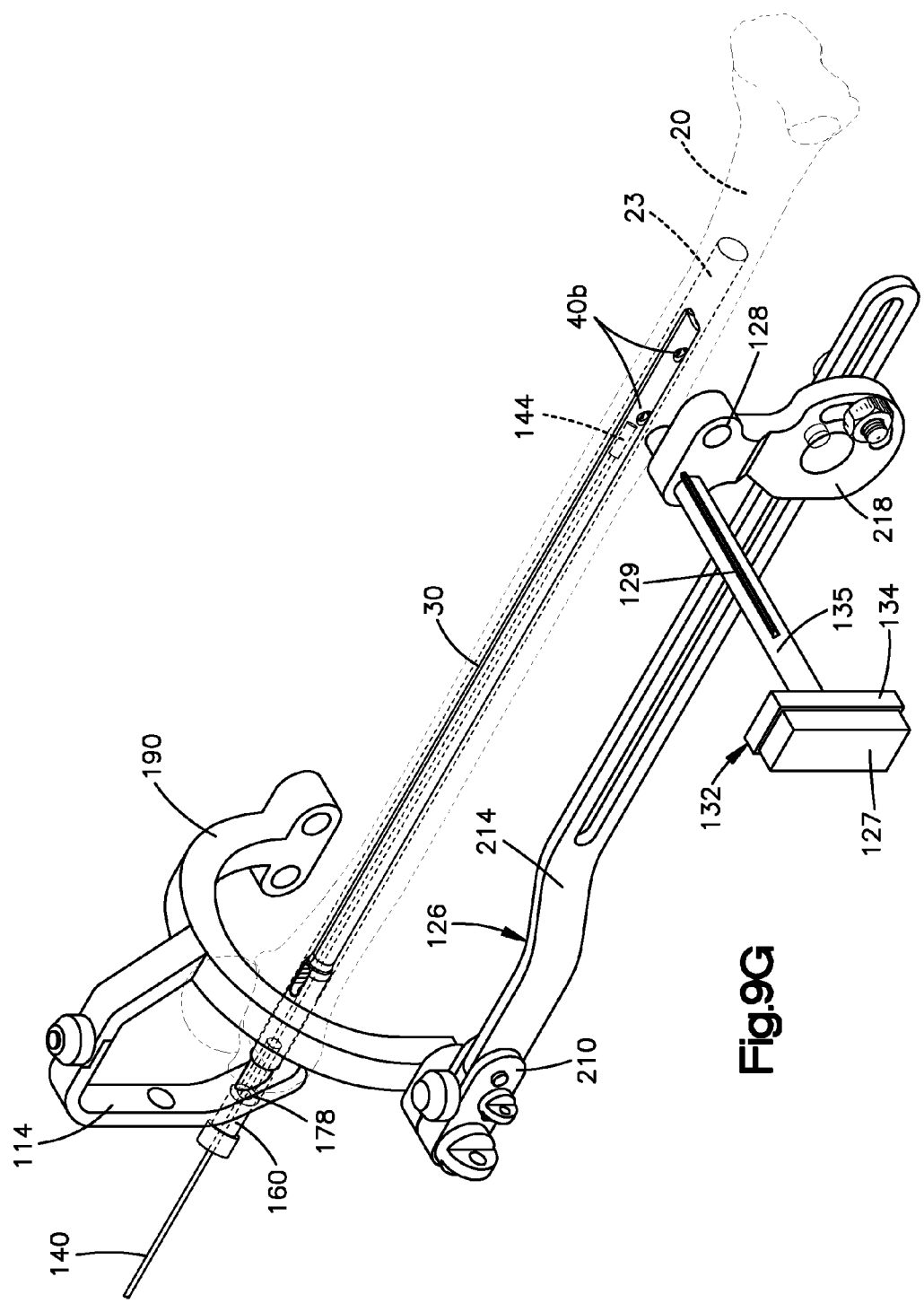
FIG. 9G is a perspective view of the system shown in FIG. 9F with the calibrated probe inserted into the channel of the intramedullary nail.

Now in reference to FIG. 9E the intramedullary nail 30 can be inserted into medullary canal 23 of the bone 20. Once fully inserted, the distal alignment guide portion 126 can be reattached to the proximal aiming arm 190 as shown in FIG. 9F. Because the medullary canal 23 can be curved the distal bone anchor holes 40b may no longer be aligned with the distal bone anchor guides 128 of the aiming guide 218. To realign the guides 128 and holes 40b, the sensor unit 134 can be attached to one of the distal bone anchor guides 128 and the probe 130 with the probe retention member 160 fixed to the probe 130 can be reinserted into the channel 138 of the intramedullary nail 30 until the shoulder 178 abuts the insertion handle 114 as shown in FIG. 9G. Because the probe 130 was previously calibrated, the source unit 144 will be in the desired position adjacent the distal bone anchor hole 40b of the intramedullary nail 30 when the shoulder 178 abuts the insertion handle 114.

Figure 9H:
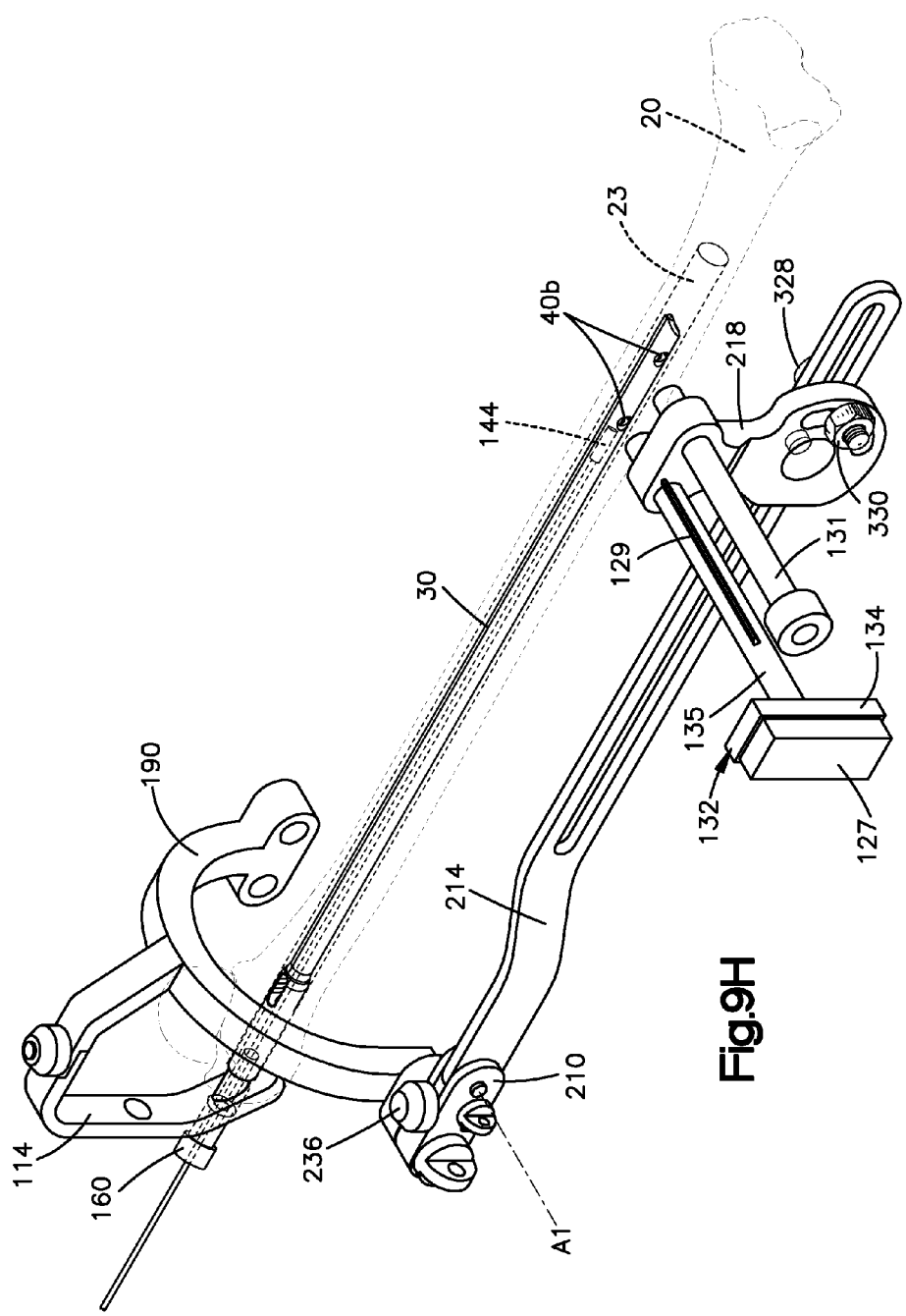
FIG. 9H is a perspective view of the system shown in FIG. 9G with the sensor unit aligned with the source unit of the probe to thereby align the bone anchor guides of the distal aiming guide with the distal bone anchor holes of the intramedullary nail.
Figure 9I:
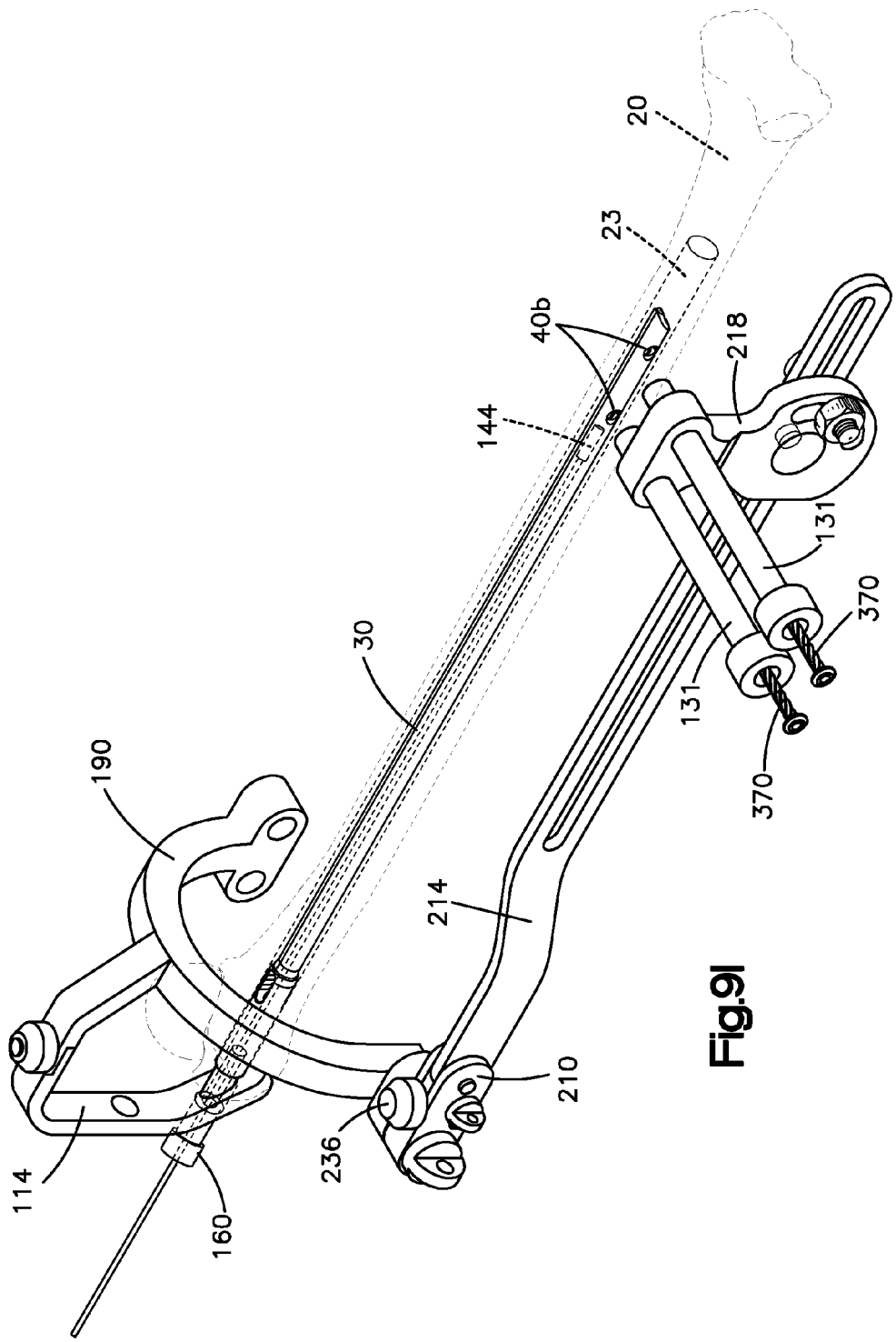
FIG. 9I is a perspective view of the system shown in FIG. 9H with a pair of sleeves attached to the distal bone anchor guides of the distal aiming guide and a pair of bone anchors being guided by the sleeves toward the aligned distal bone anchor holes of the intramedullary nail.

As shown in FIG. 9H, to realign the distal bone anchor guides 128 with the distal bone anchor holes 40b, the sensor unit 134 can be brought into alignment with the source unit 144 by adjusting the adjustment knob assembly 236 to thereby cause the aiming arm 214 to incrementally pivot about the arm pivot axis $A_1$. Furthermore, the aiming guide 218 can be positionally adjusted by translating the aiming guide 218 along the aiming arm 214, and alternatively or additionally rotating the aiming guide relative to the aiming arm 214. For example the first and second guide attachment members 328 and 330 can be loosened from each other to allow the aiming guide 218 to move relative to the aiming arm 214. It is expected, however, that once the aiming guide 218 has been aligned with the distal bone anchor holes 40b during the calibration procedure, actuation of the adjustment knob assembly 236 alone can again bring the bone anchor guides 128 of the aiming guide 218 into alignment with the distal bone anchor holes to account for bending of the nail 30 during insertion of the nail into the medullary canal 23 of the bone 20. Thus, it is easy for the user to ensure proper alignment after the insertion of the intramedullary nail 30 into the medullary canal 23. An indicator on the sensor unit 134 will indicate when the sensor unit 134 is aligned with the source unit 144. And when aligned, the bone anchor guides 128 will be aligned with the distal bone anchor holes 40b.

When aligned, the position sensor unit 134 can be removed and sleeves 131 can be attached to the bone anchor guides 128 of the aiming guide 218. A drill can then be guided by the sleeves 131 to create a hole in the bone 20 to the distal bone anchor holes 40b. And once the holes have been formed bone anchors 370 can be guided to the bone anchor holes 40b so as to affix the intramedullary nail 30 to the distal bone portion of the bone 20. Similarly, sleeves 131 can be coupled to the proximal bone anchor guides 124 so that bone anchors 370 can be guided to the proximal bone anchor holes 40a so as to affix the intramedullary nail to the proximal bone portion of the bone 20. It should be appreciated, that the steps disclosed can be performed in any order desired unless otherwise specified. Alternatively, the position sensor unit 134 can remain in the respective bone anchor guide 128, and a drilling sleeve can be inserted in other bone anchor guide 128 and the drilling is performed through the other bone anchor guide. Accordingly, the position sensor unit 134 can confirm that the bone anchor guides 128 are aligned with the distal bone anchor holes 40b while drilling. For instance, if the distal aiming arm 214 were to positionally shift slightly, the position sensor unit will detect and indicate a misalignment between the bone anchor guides 128 and the distal bone anchor holes 40b Now in reference to FIG. 10, the distal aiming guide can be configured as a distal femur aiming guide 418. The distal femur aiming guide 418 is similar to the distal humerus aiming guide 218 and includes like structure and operates in a similar manner unless otherwise described. For example the aiming guide 418 can be attached to the aiming arm 214 in a similar manner and move relative to the aiming arm 214 in a similar manner as the humerus aiming guide 218. In the illustrated embodiment the distal femur aiming guide 418 further includes an additional two holes 422 for inserting dynamic locking screws into the femur.

In reference to FIG. 11, the distal aiming arm and adjustment knob assembly can have other configurations. As shown in FIG. 11, the distal aiming arm 418 can be incrementally adjusted with an adjustment knob assembly 420. As shown, the threaded shaft 250 can include a ball 424 at its end that is received within a socket 428 defined by the distal aiming arm 418. The distal aiming arm 418 can be pivotably coupled to the pivot link 432 by a pin 440 proximal to the ball and socket joint. Therefore as the assembly 420 is actuated the distal aiming arm 418 can pivot about the pin 440 without interference from the connection between the assembly 420 and the distal aiming arm 418. It should be appreciated, however, that the pivot link, distal aiming arm, and aiming guides can have other configurations and shapes depending on the bone to be corrected. For instance, the intramedullary nail system 109 is configured for use with both a right-side long bone and a left-side long bone as described above.

While the foregoing description and drawings represent the preferred embodiment of the present invention, it will be understood that various additions, modifications, combinations and/or substitutions may be made therein without departing from the spirit and scope of the invention as defined in the accompanying claims. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. For example, features described in connection with one component may be used and/or interchanged with features described in another component. The presently disclosed embodiment is therefore to be considered in all respects as illustrative and not restrictive, the scope of the invention being indicated by the appended claims, and not limited to the foregoing description.

It will be appreciated by those skilled in the art that various modifications and alterations of the invention can be made without departing from the broad scope of the appended claims. Some of these have been discussed above and others will be apparent to those skilled in the art.

What is claimed:

1. An aiming device system configured to align at least one guide sleeve to a first distal hole of an intramedullary nail, the aiming device system comprising:
    an aiming arm configured to be operatively coupled to the intramedullary nail, the aiming arm defining a sliding support that is elongate along a first direction;
    an aiming guide including a guide body that defines at least a first bone anchor guide that is configured to retain a first guide sleeve, the aiming guide further including an attachment mechanism that is configured to mate with the sliding support to thereby attach the guide body to the aiming arm such that the guide body is (i) selectably movable along the sliding support along the first direction, and (ii) selectably rotatable relative to the aiming arm about a guide body axis that is perpendicular to the first direction,
    wherein when the first bone anchor guide retains the first guide sleeve, at least one of the selectable movement and selectable rotation of the guide body at least partially aligns the first guide sleeve with the first distal hole of the intramedullary nail,
    wherein (i) the sliding support is a slot that is elongate along the first direction, (ii) the attachment mechanism includes a pin that extends out from the guide body such that the pin defines the guide body axis, and (iii) the pin is configured to be received by the slot such that the pin is slidable within the slot,
    wherein (i) the guide body defines a curved slot and (ii) the attachment mechanism further includes first and second aiming guide attachment members, the first aiming guide attachment member being configured to extend through the slot of the aiming arm and through the curved slot of the guide body, and the second aiming guide attachment member being configured to mate with the first aiming guide attachment member to thereby attach the guide body to the aiming arm,
    wherein (i) the guide body defines a second bone anchor guide that is configured to retain a second guide sleeve that is configured to align with a second distal hole of the intramedullary nail and (ii) the aiming device system further comprising the first and second guide sleeves, each of the first and second guide sleeves including a respective bore that is configured to receive a bone anchor and guide the bone anchor to a respective one of the first and second distal holes; and
    a magnetic probe and a sensor unit, the magnetic probe having a magnet that is configured to extend into the intramedullary nail, the sensor unit being configured to be retained by the second bone anchor guide prior to the bone anchor guide retaining the second guide sleeve, wherein alignment of the sensor unit and magnet aligns the first bone anchor guide with the first distal hole of the intramedullary nail.

2. The aiming device system of claim 1, wherein the curved slot is curved such that the pin is at a center of the curve.

3. The aiming device system of claim 1, wherein (i) the first aiming guide attachment member is a screw that defines a flattened surface and the second aiming guide attachment member is a knob that threadedly receives the screw such that rotation of the knob about the screw in a first rotational direction fixes the position of the guide body relative to the aiming arm and rotation of the knob in a second rotational direction that is opposite the first rotational direction loosens the screw so as to allow the guide body to move relative to the aiming arm, and (ii) the flattened surface is received into the slot of the aiming arm and abuts the aiming arm such that the screw is rotatably fixed relative to the aiming arm when the screw is received by the slot.

4. The aiming device system of claim 1, further comprising a pivot link that is configured to be coupled to a proximal aiming arm that holds the intramedullary nail, wherein the aiming arm is coupled to the pivot link such that the aiming arm is pivotable relative to the pivot link about an arm axis.

5. The aiming device system of claim 4, further comprising a proximal aiming arm wherein the intramedullary nail is configured to be coupled to the proximal aiming arm via an insertion handle.

6. The aiming device system of claim 4, wherein (i) the aiming arm includes a threaded bore and (ii) the pivot link includes an adjustment knob that defines a threaded shaft that is configured to mate with the threaded bore such that rotation of the adjustment knob causes the aiming arm to incrementally pivot about the arm axis.

7. The aiming device system of claim 6, wherein the pivot link defines an elongate slot and further includes a locking pin that is configured to extend into the slot and couple to the adjustment knob to thereby couple the aiming arm to the pivot link.

8. The aiming device system of claim 6, wherein at least one of the selectable movement, selectable rotation of the guide body, and incremental pivoting of aiming arm aligns the first bone anchor guide with the first distal hole of the intramedullary nail.

9. The aiming device system of claim 6, wherein the threaded shaft includes a ball at its end and the aiming arm defines a socket that receives the ball.

10. The aiming device system of claim 1, wherein the magnetic probe further has an elongate shaft that extends from the magnet, the system further comprising a probe retention member that includes an elongate body and a coupler, the probe retention member defining a bore that extends through the elongate body and coupler, the bore being configured to receive the elongate shaft such that the probe retention member is slidable along the elongate shaft toward the magnet.

11. The aiming device system of claim 10, wherein the coupler includes an actuator and a compressible portion, and the actuator is configured to compress the compressible portion against the elongate shaft to thereby fix the probe retention member to the magnetic probe.

12. The aiming device system of claim 11, wherein the actuator comprises a rotatable knob threadable onto the compressible portion, so as to compress compressible segments about the elongate shaft to thereby fix the probe retention member to the magnetic probe.

13. The aiming device system of claim 11, wherein the actuator comprises a spring clip that includes a coil spring and a pair of handles that are movable so as to widen a channel defined by the coil spring such that the channel receives the compressible portion, wherein releasing the handles causes the coil spring to compress about the compressible portion to thereby fix the probe retention member to the magnetic probe.

* * * * *